US009296788B2

(12) United States Patent
Lee et al.

(10) Patent No.: US 9,296,788 B2
(45) Date of Patent: Mar. 29, 2016

(54) PRODRUG ANTI-CANCER THERAPY

(71) Applicant: Health Research Inc., Buffalo, NY (US)

(72) Inventors: Kelvin Lee, East Amherst, NY (US); Louise Carlson, East Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 30 days.

(21) Appl. No.: 14/083,695

(22) Filed: Nov. 19, 2013

(65) Prior Publication Data
US 2014/0079681 A1    Mar. 20, 2014

Related U.S. Application Data

(63) Continuation of application No. 12/820,827, filed on Jun. 22, 2010, now Pat. No. 8,609,813.

(60) Provisional application No. 61/219,220, filed on Jun. 22, 2009.

(51) Int. Cl.
*C07K 14/00* (2006.01)
*A61K 38/45* (2006.01)
*C12N 9/12* (2006.01)

(52) U.S. Cl.
CPC ............. *C07K 14/00* (2013.01); *A61K 38/45* (2013.01); *C12N 9/12* (2013.01); *C12N 9/1205* (2013.01)

(58) Field of Classification Search
CPC ...................................................... C07K 14/00
USPC ................................................. 530/350, 300
See application file for complete search history.

(56) References Cited

U.S. PATENT DOCUMENTS

| 6,004,757 A | 12/1999 | Cantley et al. |
| 6,339,151 B1 | 1/2002 | Shepard et al. |
| 2002/0123068 A1 | 9/2002 | Dwyer et al. |
| 2002/0147170 A1 | 10/2002 | Kopin et al. |
| 2003/0129169 A1 | 7/2003 | Krohn et al. |
| 2004/0096436 A1 | 5/2004 | Carson et al. |
| 2005/0187147 A1 | 8/2005 | Newman et al. |
| 2007/0141040 A1 | 6/2007 | Chen et al. |

FOREIGN PATENT DOCUMENTS

| EP | 0990442 A1 | 4/2000 |
| WO | 0025804 A2 | 5/2000 |

OTHER PUBLICATIONS

Yang, et al. Highly Efficient Green Fluorescent Protein-based Kinase Substrates, Analytical Biochemistry, 1999, vol. 266, pp. 167-173.
Wu et al., Comparison of the Intrinsic Kinase Activity and Substrate Specificity of C-Abl and Bcr-Abl, Biorganic and Medicinal Chemistry Letters, 1998, vol. 8, pp. 2279-2284.
Voss et al., The Leukaemic Oncoproteins Bcr-Abl and Tel-Abl (ETVg/Abl) Have Altered Substrate Preferences and Activate Similar Intracellular Signalling Pathways, Oncogene, 2000, vol. 19, pp. 1684-1690.
Sonnenburg et al., The Phosphoinositide-dependent Kinase, PDK-1, Phosphorylates Conventional Protein Kinase C Isozymes by a Mechanism That is Independent of Phosphoinositide 3-Kinase, The Journal of Biological Chemistry, vol. 276, Nov. 30, 2001, pp. 45289-45297.
Songyang et al., Recognition and Specificity in Protein Tyrosine Kinase-mediated Signalling, TIBS, Nov. 20, 1995, Elsevier Science Ltd., pp. 470-475.
Roeder et al., Dynamic Modeling of Imatinib-treated Chronic Myeloid Leukemia: Functional Insights and Clinical Implications, Nature Medicine, vol. 12, Oct. 2006, pp. 1181-1184.
Ren, Mechanisms of Bcr-Abl in the Pathogenesis of Chronic Myelogenous Leukaemia, Nature, Mar. 2005, vol. 5, pp. 172-183.
Jabbour, et al., Current and Emerging Treatment Options in Chronic Myeloid Leukemia, Cancer, Jun. 1, 2007, vol. 109, pp. 2171-2181.
Groffen et al., Philadelphia Chromosomal Breakpoints are Clustered Within a Limited Region, Bcr, On Chromosome 22, Cell, Jan. 1984, vol. 36, pp. 93-99.
Druker et al., Effects of a Selective Inhibitor of the Abl Tyrosine Kinase on the Growth of Bcr-Abl Positive Cells, Nature Medicine, May 1996, vol. 2, pp. 561-566.
Deninger et al., The Development of Imatinib as a Therapeutic Agent for Chronic Myeloid Leukemia, Blood, Dec. 23, 2004, vol. 105, pp. 2640-2653.
Deninger et al., Bcr-Abl Tyrosine Kinase Activity regulates the Expression of Multiple genes Implicated in the Pathogenesis of Chronic Myeloid Leukemia, Cancer Research, Apr. 1, 2000, vol. 60, pp. 2049-2055.
Cejas et al., Protein Kinase C-Beta-II Plays an essential Role in Dendritic Cell Differentiation and Autoregulates Its Own Expression, The Journal of Biological Chemistry, May 25, 2005, vol. 280, pp. 28412-28423.
Lindner, et al. Induced Dendritic Cell Differentiation of Chronic Myeloid Leukemia Blasts Is Associated with Down-Regulation of BCR-ABL, The Journal of Immunology, Aug. 15, 20013, vol. 171, No. 4, pp. 1780-1791.

*Primary Examiner* — David Lukton
(74) *Attorney, Agent, or Firm* — Hodgson Russ LLP

(57) ABSTRACT

Compositions and methods for inhibiting the growth of cancer cells are provided. The cancer cells, the growth of which is inhibited, have constitutively active Abl tyrosine kinase activity due to a t(9;22)(q34;q11) translocation which results in expression of a chimeric Bcr-Abl protein which has constitutively active Abl tyrosine kinase activity that is believed to play an important role in leukemogenesis. The compositions include a modified protein kinase C (PKC) which has an Abl tyrosine kinase target motif. The methods involve administering the modified PCK to an individual to inhibit the growth of cancer cells that have Abl tyrosine kinase activity.

5 Claims, 10 Drawing Sheets

| Clone | Sequence |
|---|---|
| WT | Arg-Phe-Ala²¹-Arg-Lys-Gly - Ala²⁵-Lys-Arg-Gln-Lys-Asn-Val |
| A1-2 | Ala²¹-Arg-Lys-*Ile* -*Tyr* - Lys-Arg-*Pro* |
| A2-1 | Ala²¹-Arg-Lys-*Ile* -*Tyr* - Lys-Arg-*Phe* |
| A3-4 | Ala²¹-Arg-Lys-*Ile* -*Tyr* - Lys-Arg-*Thr* |
| A4-6 | Ala²¹-Arg-Lys-*Ser*-*Tyr* - Lys-Arg-*Phe* |

SEQUENCE LISTING

<160> NUMBER OF SEQ ID NOS: 18

<210> SEQ ID NO 1
<211> LENGTH: 13
<212> TYPE: PRT
<213> ORGANISM: human

<400> SEQUENCE: 1

Arg Phe Ala Arg Lys Gly Ala Lys Arg Gln Lys Asn Val
1               5                   10

<210> SEQ ID NO 2
<211> LENGTH: 8
<212> TYPE: PRT
<213> ORGANISM: artificial sequence
<220> FEATURE:
<223> OTHER INFORMATION: engineered kinase motif

<400> SEQUENCE: 2

Ala Arg Lys Ile Tyr Lys Arg Pro
1               5

<210> SEQ ID NO 3
<211> LENGTH: 8
<212> TYPE: PRT
<213> ORGANISM: artificial sequence
<220> FEATURE:
<223> OTHER INFORMATION: engineered kinase target motif

<400> SEQUENCE: 3

```
Ala Arg Lys Ile Tyr Lys Arg Phe
1               5

<210> SEQ ID NO 4
<211> LENGTH: 8
<212> TYPE: PRT
<213> ORGANISM: artificial sequence
<220> FEATURE:
<223> OTHER INFORMATION: engineered kinase target motif

<400> SEQUENCE: 4

Ala Arg Lys Ile Tyr Lys Arg Thr
1               5

<210> SEQ ID NO 5
<211> LENGTH: 8
<212> TYPE: PRT
<213> ORGANISM: artificial sequence
<220> FEATURE:
<223> OTHER INFORMATION: engineered kinase target motif

<400> SEQUENCE: 5

Ala Arg Lys Ser Tyr Lys Arg Phe
1               5

<210> SEQ ID NO 6
<211> LENGTH: 8
<212> TYPE: PRT
<213> ORGANISM: artificial sequence
<220> FEATURE:
<223> OTHER INFORMATION: Abl kinase target motif concensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 6

Ala Xaa Xaa Ile Tyr Xaa Xaa Xaa
1               5

<210> SEQ ID NO 7
<211> LENGTH: 11
<212> TYPE: PRT
<213> ORGANISM: HIV

<400> SEQUENCE: 7

Tyr Gly Arg Lys Lys Arg Arg Gln Arg Arg Arg
1               5                   10

<210> SEQ ID NO 8
<211> LENGTH: 674
<212> TYPE: PRT
<213> ORGANISM: human

<400> SEQUENCE: 8

Met Ala Asp Pro Ala Ala Gly Pro Pro Ser Glu Gly Glu Glu Ser
1               5                   10                  15

Thr Val Arg Phe Ala Arg Lys Gly Ala Leu Arg Gln Lys Asn Val His
                20                  25                  30

Glu Val Lys Asn His Lys Phe Thr Ala Arg Phe Phe Lys Gln Pro Thr
            35                  40                  45

Phe Cys Ser His Cys Thr Asp Phe Ile Trp Gly Phe Gly Lys Gln Gly
```

-continued

```
               50                  55                  60
Phe Gln Cys Gln Val Cys Cys Phe Val Val His Lys Arg Cys His Glu
 65                  70                  75                  80

Phe Val Thr Phe Ser Cys Pro Gly Ala Asp Lys Gly Pro Ala Ser Asp
                 85                  90                  95

Asp Pro Arg Ser Lys His Lys Phe Lys Ile His Thr Tyr Ser Ser Pro
                100                 105                 110

Thr Phe Cys Asp His Cys Gly Ser Leu Leu Tyr Gly Leu Ile His Gln
                115                 120                 125

Gly Met Lys Cys Asp Thr Cys Met Met Asn Val His Lys Arg Cys Val
                130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                165                 170                 175

Val Arg Asp Ala Lys Asn Leu Val Pro Met Asp Pro Asn Gly Leu Ser
                180                 185                 190

Asp Pro Tyr Val Lys Leu Lys Leu Ile Pro Asp Pro Lys Ser Glu Ser
                195                 200                 205

Lys Gln Lys Thr Lys Thr Ile Lys Cys Ser Leu Asn Pro Glu Trp Asn
210                 215                 220

Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                245                 250                 255

Gly Ser Leu Ser Phe Gly Ile Ser Glu Leu Gln Lys Ala Ser Val Asp
                260                 265                 270

Gly Trp Phe Lys Leu Leu Ser Gln Glu Glu Gly Glu Tyr Phe Asn Val
                275                 280                 285

Pro Val Pro Pro Glu Gly Ser Glu Ala Asn Glu Glu Leu Arg Gln Lys
                290                 295                 300

Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
                325                 330                 335

Met Lys Leu Thr Asp Phe Asn Phe Leu Met Val Leu Gly Lys Gly Ser
                340                 345                 350

Phe Gly Lys Val Met Leu Ser Glu Arg Lys Gly Thr Asp Glu Leu Tyr
                355                 360                 365

Ala Val Lys Ile Leu Lys Lys Asp Val Val Ile Gln Asp Asp Asp Val
370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
                405                 410                 415

Tyr Phe Val Met Glu Tyr Val Asn Gly Gly Asp Leu Met Tyr His Ile
                420                 425                 430

Gln Gln Val Gly Arg Phe Lys Glu Pro His Ala Val Phe Tyr Ala Ala
                435                 440                 445

Glu Ile Ala Ile Gly Leu Phe Phe Leu Gln Ser Lys Gly Ile Ile Tyr
                450                 455                 460

Arg Asp Leu Lys Leu Asp Asn Val Met Leu Asp Ser Glu Gly His Ile
465                 470                 475                 480
```

```
Lys Ile Ala Asp Phe Gly Met Cys Lys Glu Asn Ile Trp Asp Gly Val
                485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
        515                 520                 525

Val Leu Leu Tyr Glu Met Leu Ala Gly Gln Ala Pro Phe Glu Gly Glu
    530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
                565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
        595                 600                 605

Glu Arg Lys Glu Ile Gln Pro Pro Tyr Lys Pro Lys Ala Cys Gly Arg
    610                 615                 620

Asn Ala Glu Asn Phe Asp Arg Phe Phe Thr Arg His Pro Pro Val Leu
625                 630                 635                 640

Thr Pro Pro Asp Gln Glu Val Ile Arg Asn Ile Asp Gln Ser Glu Phe
                645                 650                 655

Glu Gly Phe Ser Phe Val Asn Ser Glu Phe Leu Lys Pro Glu Val Lys
            660                 665                 670

Ser Ala

<210> SEQ ID NO 9
<211> LENGTH: 920
<212> TYPE: PRT
<213> ORGANISM: artificial
<220> FEATURE:
<223> OTHER INFORMATION: PKC Beta II GFP fusion

<400> SEQUENCE: 9

Met Ala Asp Pro Ala Ala Gly Pro Pro Pro Ser Glu Gly Glu Glu Ser
1               5                   10                  15

Thr Val Arg Phe Ala Arg Lys Gly Ala Leu Arg Gln Lys Asn Val His
            20                  25                  30

Glu Val Lys Asn His Lys Phe Thr Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Ala Ser Asp
                85                  90                  95

Asp Pro Arg Ser Lys His Lys Phe Lys Ile His Thr Tyr Ser Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Met Met Asn Val His Lys Arg Cys Val
    130                 135                 140

Met Asn Val Pro Ser Leu Cys Gly Thr Asp His Thr Glu Arg Arg Gly
145                 150                 155                 160
```

-continued

```
Arg Ile Tyr Ile Gln Ala His Ile Asp Arg Asp Val Leu Ile Val Leu
                165                 170                 175
Val Arg Asp Ala Lys Asn Leu Val Pro Met Asp Pro Asn Gly Leu Ser
            180                 185                 190
Asp Pro Tyr Val Lys Leu Lys Leu Ile Pro Asp Pro Lys Ser Glu Ser
        195                 200                 205
Lys Gln Lys Thr Lys Thr Ile Lys Cys Ser Leu Asn Pro Glu Trp Asn
    210                 215                 220
Glu Thr Phe Arg Phe Gln Leu Lys Glu Ser Asp Lys Asp Arg Arg Leu
225                 230                 235                 240
Ser Val Glu Ile Trp Asp Trp Asp Leu Thr Ser Arg Asn Asp Phe Met
                245                 250                 255
Gly Ser Leu Ser Phe Gly Ile Ser Glu Leu Gln Lys Ala Ser Val Asp
            260                 265                 270
Gly Trp Phe Lys Leu Leu Ser Gln Glu Glu Gly Glu Tyr Phe Asn Val
        275                 280                 285
Pro Val Pro Pro Glu Gly Ser Glu Ala Asn Glu Glu Leu Arg Gln Lys
    290                 295                 300
Phe Glu Arg Ala Lys Ile Ser Gln Gly Thr Lys Val Pro Glu Glu Lys
305                 310                 315                 320
Thr Thr Asn Thr Val Ser Lys Phe Asp Asn Asn Gly Asn Arg Asp Arg
                325                 330                 335
Met Lys Leu Thr Asp Phe Asn Phe Leu Met Val Leu Gly Lys Gly Ser
            340                 345                 350
Phe Gly Lys Val Met Leu Ser Glu Arg Lys Gly Thr Asp Glu Leu Tyr
        355                 360                 365
Ala Val Lys Ile Leu Lys Lys Asp Val Val Ile Gln Asp Asp Asp Val
    370                 375                 380
Glu Cys Thr Met Val Glu Lys Arg Val Leu Ala Leu Pro Gly Lys Pro
385                 390                 395                 400
Pro Phe Leu Thr Gln Leu His Ser Cys Phe Gln Thr Met Asp Arg Leu
                405                 410                 415
Tyr Phe Val Met Glu Tyr Val Asn Gly Gly Asp Leu Met Tyr His Ile
            420                 425                 430
Gln Gln Val Gly Arg Phe Lys Glu Pro His Ala Val Phe Tyr Ala Ala
        435                 440                 445
Glu Ile Ala Ile Gly Leu Phe Phe Leu Gln Ser Lys Gly Ile Ile Tyr
    450                 455                 460
Arg Asp Leu Lys Leu Asp Asn Val Met Leu Asp Ser Glu Gly His Ile
465                 470                 475                 480
Lys Ile Ala Asp Phe Gly Met Cys Lys Glu Asn Ile Trp Asp Gly Val
                485                 490                 495
Thr Thr Lys Thr Phe Cys Gly Thr Pro Asp Tyr Ile Ala Pro Glu Ile
            500                 505                 510
Ile Ala Tyr Gln Pro Tyr Gly Lys Ser Val Asp Trp Trp Ala Phe Gly
        515                 520                 525
Val Leu Leu Tyr Glu Met Leu Ala Gly Gln Ala Pro Phe Glu Gly Glu
    530                 535                 540
Asp Glu Asp Glu Leu Phe Gln Ser Ile Met Glu His Asn Val Ala Tyr
545                 550                 555                 560
Pro Lys Ser Met Ser Lys Glu Ala Val Ala Ile Cys Lys Gly Leu Met
                565                 570                 575
Thr Lys His Pro Gly Lys Arg Leu Gly Cys Gly Pro Glu Gly Glu Arg
```

```
                    580                 585                 590
Asp Ile Lys Glu His Ala Phe Phe Arg Tyr Ile Asp Trp Glu Lys Leu
                595                 600                 605

Glu Arg Lys Glu Ile Gln Pro Pro Tyr Lys Pro Lys Ala Cys Gly Arg
            610                 615                 620

Asn Ala Glu Asn Phe Asp Arg Phe Phe Thr Arg His Pro Pro Val Leu
625                 630                 635                 640

Thr Pro Pro Asp Gln Glu Val Ile Arg Asn Ile Asp Gln Ser Glu Phe
                645                 650                 655

Glu Gly Phe Ser Phe Val Asn Ser Glu Phe Leu Lys Pro Glu Val Lys
            660                 665                 670

Ser Ala Arg Asp Pro Pro Val Ala Thr Met Val Ser Lys Gly Glu Glu
        675                 680                 685

Leu Phe Thr Gly Val Val Pro Ile Leu Val Glu Leu Asp Gly Asp Val
    690                 695                 700

Asn Gly His Lys Phe Ser Val Ser Gly Glu Gly Glu Gly Asp Ala Thr
705                 710                 715                 720

Tyr Gly Lys Leu Thr Leu Lys Phe Ile Cys Thr Thr Gly Lys Leu Pro
                725                 730                 735

Val Pro Trp Pro Thr Leu Val Thr Thr Leu Thr Tyr Gly Val Gln Cys
            740                 745                 750

Phe Ser Arg Tyr Pro Asp His Met Lys Gln His Asp Phe Phe Lys Ser
        755                 760                 765

Ala Met Pro Glu Gly Tyr Val Gln Glu Arg Thr Ile Phe Phe Lys Asp
    770                 775                 780

Asp Gly Asn Tyr Lys Thr Arg Ala Glu Val Lys Phe Glu Gly Asp Thr
785                 790                 795                 800

Leu Val Asn Arg Ile Glu Leu Lys Gly Ile Asp Phe Lys Glu Asp Gly
                805                 810                 815

Asn Ile Leu Gly His Lys Leu Glu Tyr Asn Tyr Asn Ser His Asn Val
            820                 825                 830

Tyr Ile Met Ala Asp Lys Gln Lys Asn Gly Ile Lys Val Asn Phe Lys
        835                 840                 845

Ile Arg His Asn Ile Glu Asp Gly Ser Val Gln Leu Ala Asp His Tyr
    850                 855                 860

Gln Gln Asn Thr Pro Ile Gly Asp Gly Pro Val Leu Leu Pro Asp Asn
865                 870                 875                 880

His Tyr Leu Ser Thr Gln Ser Ala Leu Ser Lys Asp Pro Asn Glu Lys
                885                 890                 895

Arg Asp His Met Val Leu Leu Glu Phe Val Thr Ala Ala Gly Ile Thr
            900                 905                 910

Leu Gly Met Asp Glu Leu Tyr Lys
        915                 920

<210> SEQ ID NO 10
<211> LENGTH: 920
<212> TYPE: PRT
<213> ORGANISM: artificial sequence
<220> FEATURE:
<223> OTHER INFORMATION: PKC Beta II GFP A1-2 fusion protein

<400> SEQUENCE: 10

Met Ala Asp Pro Ala Ala Gly Pro Pro Ser Glu Gly Glu Glu Ser
1               5                   10                  15

Thr Val Arg Phe Ala Arg Lys Ile Tyr Leu Arg Pro Lys Asn Val His
```

-continued

```
                20                  25                  30
Glu Val Lys Asn His Lys Phe Thr Ala Arg Phe Phe Lys Gln Pro Thr
             35                  40                  45
Phe Cys Ser His Cys Thr Asp Phe Ile Trp Gly Phe Lys Gln Gly
         50                  55                  60
Phe Gln Cys Gln Val Cys Cys Phe Val Val His Lys Arg Cys His Glu
 65                  70                  75                  80
Phe Val Thr Phe Ser Cys Pro Gly Ala Asp Lys Gly Pro Ala Ser Asp
                 85                  90                  95
Asp Pro Arg Ser Lys His Lys Phe Lys Ile His Thr Tyr Ser Ser Pro
             100                 105                 110
Thr Phe Cys Asp His Cys Gly Ser Leu Leu Tyr Gly Leu Ile His Gln
         115                 120                 125
Gly Met Lys Cys Asp Thr Cys Met Met Asn Val His Lys Arg Cys Val
     130                 135                 140
Met Asn Val Pro Ser Leu Cys Gly Thr Asp His Thr Glu Arg Arg Gly
145                 150                 155                 160
Arg Ile Tyr Ile Gln Ala His Ile Asp Arg Asp Val Leu Ile Val Leu
                 165                 170                 175
Val Arg Asp Ala Lys Asn Leu Val Pro Met Asp Pro Asn Gly Leu Ser
             180                 185                 190
Asp Pro Tyr Val Lys Leu Lys Leu Ile Pro Asp Pro Lys Ser Glu Ser
         195                 200                 205
Lys Gln Lys Thr Lys Thr Ile Lys Cys Ser Leu Asn Pro Glu Trp Asn
     210                 215                 220
Glu Thr Phe Arg Phe Gln Leu Lys Glu Ser Asp Lys Asp Arg Arg Leu
225                 230                 235                 240
Ser Val Glu Ile Trp Asp Trp Asp Leu Thr Ser Arg Asn Asp Phe Met
                 245                 250                 255
Gly Ser Leu Ser Phe Gly Ile Ser Glu Leu Gln Lys Ala Ser Val Asp
             260                 265                 270
Gly Trp Phe Lys Leu Leu Ser Gln Glu Glu Gly Glu Tyr Phe Asn Val
         275                 280                 285
Pro Val Pro Pro Glu Gly Ser Glu Ala Asn Glu Glu Leu Arg Gln Lys
     290                 295                 300
Phe Glu Arg Ala Lys Ile Ser Gln Gly Thr Lys Val Pro Glu Glu Lys
305                 310                 315                 320
Thr Thr Asn Thr Val Ser Lys Phe Asp Asn Asn Gly Asn Arg Asp Arg
                 325                 330                 335
Met Lys Leu Thr Asp Phe Asn Phe Leu Met Val Leu Gly Lys Gly Ser
             340                 345                 350
Phe Gly Lys Val Met Leu Ser Glu Arg Lys Gly Thr Asp Glu Leu Tyr
         355                 360                 365
Ala Val Lys Ile Leu Lys Lys Asp Val Ile Gln Asp Asp Val
     370                 375                 380
Glu Cys Thr Met Val Glu Lys Arg Val Leu Ala Leu Pro Gly Lys Pro
385                 390                 395                 400
Pro Phe Leu Thr Gln Leu His Ser Cys Phe Gln Thr Met Asp Arg Leu
                 405                 410                 415
Tyr Phe Val Met Glu Tyr Val Asn Gly Gly Asp Leu Met Tyr His Ile
             420                 425                 430
Gln Gln Val Gly Arg Phe Lys Glu Pro His Ala Val Phe Tyr Ala Ala
         435                 440                 445
```

```
Glu Ile Ala Ile Gly Leu Phe Phe Leu Gln Ser Lys Gly Ile Ile Tyr
    450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
                485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
        515                 520                 525

Val Leu Leu Tyr Glu Met Leu Ala Gly Gln Ala Pro Phe Glu Gly Glu
    530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
                565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
        595                 600                 605

Glu Arg Lys Glu Ile Gln Pro Pro Tyr Lys Pro Lys Ala Cys Gly Arg
    610                 615                 620

Asn Ala Glu Asn Phe Asp Arg Phe Phe Thr Arg His Pro Pro Val Leu
625                 630                 635                 640

Thr Pro Pro Asp Gln Glu Val Ile Arg Asn Ile Asp Gln Ser Glu Phe
                645                 650                 655

Glu Gly Phe Ser Phe Val Asn Ser Glu Phe Leu Lys Pro Glu Val Lys
            660                 665                 670

Ser Ala Arg Asp Pro Pro Val Ala Thr Met Val Ser Lys Gly Glu Glu
        675                 680                 685

Leu Phe Thr Gly Val Val Pro Ile Leu Val Glu Leu Asp Gly Asp Val
    690                 695                 700

Asn Gly His Lys Phe Ser Val Ser Gly Glu Gly Glu Gly Asp Ala Thr
705                 710                 715                 720

Tyr Gly Lys Leu Thr Leu Lys Phe Ile Cys Thr Thr Gly Lys Leu Pro
                725                 730                 735

Val Pro Trp Pro Thr Leu Val Thr Thr Leu Thr Tyr Gly Val Gln Cys
            740                 745                 750

Phe Ser Arg Tyr Pro Asp His Met Lys Gln His Asp Phe Phe Lys Ser
        755                 760                 765

Ala Met Pro Glu Gly Tyr Val Gln Glu Arg Thr Ile Phe Phe Lys Asp
    770                 775                 780

Asp Gly Asn Tyr Lys Thr Arg Ala Glu Val Lys Phe Glu Gly Asp Thr
785                 790                 795                 800

Leu Val Asn Arg Ile Glu Leu Lys Gly Ile Asp Phe Lys Glu Asp Gly
                805                 810                 815

Asn Ile Leu Gly His Lys Leu Glu Tyr Asn Tyr Asn Ser His Asn Val
            820                 825                 830

Tyr Ile Met Ala Asp Lys Gln Lys Asn Gly Ile Lys Val Asn Phe Lys
        835                 840                 845

Ile Arg His Asn Ile Glu Asp Gly Ser Val Gln Leu Ala Asp His Tyr
    850                 855                 860
```

```
Gln Gln Asn Thr Pro Ile Gly Asp Gly Pro Val Leu Leu Pro Asp Asn
865                 870                 875                 880

His Tyr Leu Ser Thr Gln Ser Ala Leu Ser Lys Asp Pro Asn Glu Lys
                885                 890                 895

Arg Asp His Met Val Leu Leu Glu Phe Val Thr Ala Ala Gly Ile Thr
            900                 905                 910

Leu Gly Met Asp Glu Leu Tyr Lys
            915                 920

<210> SEQ ID NO 11
<211> LENGTH: 920
<212> TYPE: PRT
<213> ORGANISM: artificial sequence
<220> FEATURE:
<223> OTHER INFORMATION: PKC Beta II GFP A2-1 fusion protein

<400> SEQUENCE: 11

Met Ala Asp Pro Ala Ala Gly Pro Pro Ser Glu Gly Glu Glu Ser
1               5                   10                  15

Thr Val Arg Phe Ala Arg Lys Ile Tyr Leu Arg Phe Lys Asn Val His
                20                  25                  30

Glu Val Lys Asn His Lys Phe Thr Ala Arg Phe Phe Lys Gln Pro Thr
            35                  40                  45

Phe Cys Ser His Cys Thr Asp Phe Ile Trp Gly Phe Gly Lys Gln Gly
50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Ala Ser Asp
                85                  90                  95

Asp Pro Arg Ser Lys His Lys Phe Lys Ile His Thr Tyr Ser Ser Pro
            100                 105                 110

Thr Phe Cys Asp His Cys Gly Ser Leu Leu Tyr Gly Leu Ile His Gln
            115                 120                 125

Gly Met Lys Cys Asp Thr Cys Met Met Asn Val His Lys Arg Cys Val
130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                165                 170                 175

Val Arg Asp Ala Lys Asn Leu Val Pro Met Asp Pro Asn Gly Leu Ser
            180                 185                 190

Asp Pro Tyr Val Lys Leu Lys Leu Ile Pro Asp Pro Lys Ser Glu Ser
        195                 200                 205

Lys Gln Lys Thr Lys Thr Ile Lys Cys Ser Leu Asn Pro Glu Trp Asn
210                 215                 220

Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                245                 250                 255

Gly Ser Leu Ser Phe Gly Ile Ser Glu Leu Gln Lys Ala Ser Val Asp
            260                 265                 270

Gly Trp Phe Lys Leu Leu Ser Gln Glu Glu Gly Glu Tyr Phe Asn Val
        275                 280                 285

Pro Val Pro Pro Glu Gly Ser Glu Ala Asn Glu Glu Leu Arg Gln Lys
    290                 295                 300
```

```
Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
            325                 330                 335

Met Lys Leu Thr Asp Phe Asn Phe Leu Met Val Leu Gly Lys Gly Ser
            340                 345                 350

Phe Gly Lys Val Met Leu Ser Glu Arg Lys Gly Thr Asp Glu Leu Tyr
        355                 360                 365

Ala Val Lys Ile Leu Lys Lys Asp Val Val Ile Gln Asp Asp Asp Val
        370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
            405                 410                 415

Tyr Phe Val Met Glu Tyr Val Asn Gly Gly Asp Leu Met Tyr His Ile
            420                 425                 430

Gln Gln Val Gly Arg Phe Lys Glu Pro His Ala Val Phe Tyr Ala Ala
        435                 440                 445

Glu Ile Ala Ile Gly Leu Phe Phe Leu Gln Ser Lys Gly Ile Ile Tyr
450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
            485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
        515                 520                 525

Val Leu Leu Tyr Glu Met Leu Ala Gly Gln Ala Pro Phe Glu Gly Glu
        530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
            565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
        595                 600                 605

Glu Arg Lys Glu Ile Gln Pro Pro Tyr Lys Pro Lys Ala Cys Gly Arg
        610                 615                 620

Asn Ala Glu Asn Phe Asp Arg Phe Phe Thr Arg His Pro Pro Val Leu
625                 630                 635                 640

Thr Pro Pro Asp Gln Glu Val Ile Arg Asn Ile Asp Gln Ser Glu Phe
            645                 650                 655

Glu Gly Phe Ser Phe Val Asn Ser Glu Phe Leu Lys Pro Glu Val Lys
            660                 665                 670

Ser Ala Arg Asp Pro Val Ala Thr Met Val Ser Lys Gly Glu Glu
        675                 680                 685

Leu Phe Thr Gly Val Val Pro Ile Leu Val Glu Leu Asp Gly Asp Val
        690                 695                 700

Asn Gly His Lys Phe Ser Val Ser Gly Glu Gly Glu Gly Asp Ala Thr
705                 710                 715                 720

Tyr Gly Lys Leu Thr Leu Lys Phe Ile Cys Thr Thr Gly Lys Leu Pro
```

```
                725                 730                 735
Val Pro Trp Pro Thr Leu Val Thr Thr Leu Thr Tyr Gly Val Gln Cys
            740                 745                 750

Phe Ser Arg Tyr Pro Asp His Met Lys Gln His Asp Phe Phe Lys Ser
            755                 760                 765

Ala Met Pro Glu Gly Tyr Val Gln Glu Arg Thr Ile Phe Phe Lys Asp
            770                 775                 780

Asp Gly Asn Tyr Lys Thr Arg Ala Glu Val Lys Phe Glu Gly Asp Thr
785                 790                 795                 800

Leu Val Asn Arg Ile Glu Leu Lys Gly Ile Asp Phe Lys Glu Asp Gly
            805                 810                 815

Asn Ile Leu Gly His Lys Leu Glu Tyr Asn Tyr Asn Ser His Asn Val
            820                 825                 830

Tyr Ile Met Ala Asp Lys Gln Lys Asn Gly Ile Lys Val Asn Phe Lys
            835                 840                 845

Ile Arg His Asn Ile Glu Asp Gly Ser Val Gln Leu Ala Asp His Tyr
            850                 855                 860

Gln Gln Asn Thr Pro Ile Gly Asp Gly Pro Val Leu Leu Pro Asp Asn
865                 870                 875                 880

His Tyr Leu Ser Thr Gln Ser Ala Leu Ser Lys Asp Pro Asn Glu Lys
            885                 890                 895

Arg Asp His Met Val Leu Leu Glu Phe Val Thr Ala Ala Gly Ile Thr
            900                 905                 910

Leu Gly Met Asp Glu Leu Tyr Lys
            915                 920

<210> SEQ ID NO 12
<211> LENGTH: 920
<212> TYPE: PRT
<213> ORGANISM: artificial sequence
<220> FEATURE:
<223> OTHER INFORMATION: PKC Beta II GFP A3-4 fusion protein

<400> SEQUENCE: 12

Met Ala Asp Pro Ala Ala Gly Pro Pro Ser Glu Gly Glu Glu Ser
1               5                  10                  15

Thr Val Arg Phe Ala Arg Lys Ile Tyr Leu Arg Thr Lys Asn Val His
            20                  25                  30

Glu Val Lys Asn His Lys Phe Thr Ala Arg Phe Phe Lys Gln Pro Thr
            35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Ala Ser Asp
            85                  90                  95

Asp Pro Arg Ser Lys His Lys Phe Lys Ile His Thr Tyr Ser Ser Pro
            100                 105                 110

Thr Phe Cys Asp His Cys Gly Ser Leu Leu Tyr Gly Leu Ile His Gln
            115                 120                 125

Gly Met Lys Cys Asp Thr Cys Met Met Asn Val His Lys Arg Cys Val
            130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
```

-continued

```
                165                 170                 175
Val Arg Asp Ala Lys Asn Leu Val Pro Met Asp Pro Asn Gly Leu Ser
            180                 185                 190
Asp Pro Tyr Val Lys Leu Lys Leu Ile Pro Asp Pro Lys Ser Glu Ser
            195                 200                 205
Lys Gln Lys Thr Lys Thr Ile Lys Cys Ser Leu Asn Pro Glu Trp Asn
210                 215                 220
Glu Thr Phe Arg Phe Gln Leu Lys Glu Ser Asp Lys Asp Arg Arg Leu
225                 230                 235                 240
Ser Val Glu Ile Trp Asp Trp Asp Leu Thr Ser Arg Asn Asp Phe Met
                245                 250                 255
Gly Ser Leu Ser Phe Gly Ile Ser Glu Leu Gln Lys Ala Ser Val Asp
                260                 265                 270
Gly Trp Phe Lys Leu Leu Ser Gln Glu Glu Gly Glu Tyr Phe Asn Val
            275                 280                 285
Pro Val Pro Pro Glu Gly Ser Glu Ala Asn Glu Glu Leu Arg Gln Lys
            290                 295                 300
Phe Glu Arg Ala Lys Ile Ser Gln Gly Thr Lys Val Pro Glu Glu Lys
305                 310                 315                 320
Thr Thr Asn Thr Val Ser Lys Phe Asp Asn Asn Gly Asn Arg Asp Arg
                325                 330                 335
Met Lys Leu Thr Asp Phe Asn Phe Leu Met Val Leu Gly Lys Gly Ser
                340                 345                 350
Phe Gly Lys Val Met Leu Ser Glu Arg Lys Gly Thr Asp Glu Leu Tyr
            355                 360                 365
Ala Val Lys Ile Leu Lys Lys Asp Val Val Ile Gln Asp Asp Asp Val
            370                 375                 380
Glu Cys Thr Met Val Glu Lys Arg Val Leu Ala Leu Pro Gly Lys Pro
385                 390                 395                 400
Pro Phe Leu Thr Gln Leu His Ser Cys Phe Gln Thr Met Asp Arg Leu
                405                 410                 415
Tyr Phe Val Met Glu Tyr Val Asn Gly Gly Asp Leu Met Tyr His Ile
                420                 425                 430
Gln Gln Val Gly Arg Phe Lys Glu Pro His Ala Val Phe Tyr Ala Ala
            435                 440                 445
Glu Ile Ala Ile Gly Leu Phe Phe Leu Gln Ser Lys Gly Ile Ile Tyr
            450                 455                 460
Arg Asp Leu Lys Leu Asp Asn Val Met Leu Asp Ser Glu Gly His Ile
465                 470                 475                 480
Lys Ile Ala Asp Phe Gly Met Cys Lys Glu Asn Ile Trp Asp Gly Val
                485                 490                 495
Thr Thr Lys Thr Phe Cys Gly Thr Pro Asp Tyr Ile Ala Pro Glu Ile
                500                 505                 510
Ile Ala Tyr Gln Pro Tyr Gly Lys Ser Val Asp Trp Trp Ala Phe Gly
            515                 520                 525
Val Leu Leu Tyr Glu Met Leu Ala Gly Gln Ala Pro Phe Glu Gly Glu
            530                 535                 540
Asp Glu Asp Glu Leu Phe Gln Ser Ile Met Glu His Asn Val Ala Tyr
545                 550                 555                 560
Pro Lys Ser Met Ser Lys Glu Ala Val Ala Ile Cys Lys Gly Leu Met
                565                 570                 575
Thr Lys His Pro Gly Lys Arg Leu Gly Cys Gly Pro Glu Gly Glu Arg
                580                 585                 590
```

Asp Ile Lys Glu His Ala Phe Phe Arg Tyr Ile Asp Trp Glu Lys Leu
            595                 600                 605

Glu Arg Lys Glu Ile Gln Pro Pro Tyr Lys Pro Lys Ala Cys Gly Arg
610                 615                 620

Asn Ala Glu Asn Phe Asp Arg Phe Phe Thr Arg His Pro Pro Val Leu
625                 630                 635                 640

Thr Pro Pro Asp Gln Glu Val Ile Arg Asn Ile Asp Gln Ser Glu Phe
                645                 650                 655

Glu Gly Phe Ser Phe Val Asn Ser Gly Phe Leu Lys Pro Glu Val Lys
                660                 665                 670

Ser Ala Arg Asp Pro Pro Val Ala Thr Met Val Ser Lys Gly Glu Glu
            675                 680                 685

Leu Phe Thr Gly Val Val Pro Ile Leu Val Glu Leu Asp Gly Asp Val
            690                 695                 700

Asn Gly His Lys Phe Ser Val Ser Gly Glu Gly Glu Gly Asp Ala Thr
705                 710                 715                 720

Tyr Gly Lys Leu Thr Leu Lys Phe Ile Cys Thr Thr Gly Lys Leu Pro
                725                 730                 735

Val Pro Trp Pro Thr Leu Val Thr Thr Leu Thr Tyr Gly Val Gln Cys
            740                 745                 750

Phe Ser Arg Tyr Pro Asp His Met Lys Gln His Asp Phe Phe Lys Ser
            755                 760                 765

Ala Met Pro Glu Gly Tyr Val Gln Glu Arg Thr Ile Phe Phe Lys Asp
            770                 775                 780

Asp Gly Asn Tyr Lys Thr Arg Ala Glu Val Lys Phe Glu Gly Asp Thr
785                 790                 795                 800

Leu Val Asn Arg Ile Glu Leu Lys Gly Ile Asp Phe Lys Glu Asp Gly
                805                 810                 815

Asn Ile Leu Gly His Lys Leu Glu Tyr Asn Tyr Asn Ser His Asn Val
            820                 825                 830

Tyr Ile Met Ala Asp Lys Gln Lys Asn Gly Ile Lys Val Asn Phe Lys
            835                 840                 845

Ile Arg His Asn Ile Glu Asp Gly Ser Val Gln Leu Ala Asp His Tyr
            850                 855                 860

Gln Gln Asn Thr Pro Ile Gly Asp Gly Pro Val Leu Leu Pro Asp Asn
865                 870                 875                 880

His Tyr Leu Ser Thr Gln Ser Ala Leu Ser Lys Asp Pro Asn Glu Lys
                885                 890                 895

Arg Asp His Met Val Leu Leu Glu Phe Val Thr Ala Ala Gly Ile Thr
            900                 905                 910

Leu Gly Met Asp Glu Leu Tyr Lys
            915                 920

<210> SEQ ID NO 13
<211> LENGTH: 920
<212> TYPE: PRT
<213> ORGANISM: artificial sequence
<220> FEATURE:
<223> OTHER INFORMATION: PKC Beta II GFP A4-6 fusion protein

<400> SEQUENCE: 13

Met Ala Asp Pro Ala Ala Gly Pro Pro Ser Glu Gly Glu Glu Ser
1               5                   10                  15

Thr Val Arg Phe Ala Arg Lys Ser Tyr Leu Arg Phe Lys Asn Val His
                20                  25                  30

-continued

```
Glu Val Lys Asn His Lys Phe Thr Ala Arg Phe Phe Lys Gln Pro Thr
         35                  40                  45

Phe Cys Ser His Cys Thr Asp Phe Ile Trp Gly Phe Gly Lys Gln Gly
 50                  55                  60

Phe Gln Cys Gln Val Cys Cys Phe Val Val His Lys Arg Cys His Glu
 65                  70                  75                  80

Phe Val Thr Phe Ser Cys Pro Gly Ala Asp Lys Gly Pro Ala Ser Asp
                 85                  90                  95

Asp Pro Arg Ser Lys His Lys Phe Lys Ile His Thr Tyr Ser Ser Pro
             100                 105                 110

Thr Phe Cys Asp His Cys Gly Ser Leu Leu Tyr Gly Leu Ile His Gln
         115                 120                 125

Gly Met Lys Cys Asp Thr Cys Met Met Asn Val His Lys Arg Cys Val
     130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                 165                 170                 175

Val Arg Asp Ala Lys Asn Leu Val Pro Met Asp Pro Asn Gly Leu Ser
             180                 185                 190

Asp Pro Tyr Val Lys Leu Lys Leu Ile Pro Asp Pro Lys Ser Glu Ser
         195                 200                 205

Lys Gln Lys Thr Lys Thr Ile Lys Cys Ser Leu Asn Pro Glu Trp Asn
     210                 215                 220

Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                 245                 250                 255

Gly Ser Leu Ser Phe Gly Ile Ser Glu Leu Gln Lys Ala Ser Val Asp
             260                 265                 270

Gly Trp Phe Lys Leu Leu Ser Gln Glu Glu Gly Glu Tyr Phe Asn Val
         275                 280                 285

Pro Val Pro Pro Glu Gly Ser Glu Ala Asn Glu Glu Leu Arg Gln Lys
     290                 295                 300

Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
                 325                 330                 335

Met Lys Leu Thr Asp Phe Asn Phe Leu Met Val Leu Gly Lys Gly Ser
             340                 345                 350

Phe Gly Lys Val Met Leu Ser Glu Arg Lys Gly Thr Asp Glu Leu Tyr
         355                 360                 365

Ala Val Lys Ile Leu Lys Lys Asp Val Ile Gln Asp Asp Asp Val
     370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
                 405                 410                 415

Tyr Phe Val Met Glu Tyr Val Asn Gly Gly Asp Leu Met Tyr His Ile
             420                 425                 430

Gln Gln Val Gly Arg Phe Lys Glu Pro His Ala Val Phe Tyr Ala Ala
         435                 440                 445
```

-continued

Glu Ile Ala Ile Gly Leu Phe Phe Leu Gln Ser Lys Gly Ile Ile Tyr
            450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
                485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
            515                 520                 525

Val Leu Leu Tyr Glu Met Leu Ala Gly Gln Ala Pro Phe Glu Gly Glu
530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
                565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
            595                 600                 605

Glu Arg Lys Glu Ile Gln Pro Pro Tyr Lys Pro Lys Ala Cys Gly Arg
610                 615                 620

Asn Ala Glu Asn Phe Asp Arg Phe Phe Thr Arg His Pro Pro Val Leu
625                 630                 635                 640

Thr Pro Pro Asp Gln Glu Val Ile Arg Asn Ile Asp Gln Ser Glu Phe
                645                 650                 655

Glu Gly Phe Ser Phe Val Asn Ser Glu Phe Leu Lys Pro Glu Val Lys
            660                 665                 670

Ser Ala Arg Asp Pro Pro Val Ala Thr Met Val Ser Lys Gly Glu Glu
            675                 680                 685

Leu Phe Thr Gly Val Val Pro Ile Leu Val Glu Leu Asp Gly Asp Val
    690                 695                 700

Asn Gly His Lys Phe Ser Val Ser Gly Glu Gly Glu Gly Asp Ala Thr
705                 710                 715                 720

Tyr Gly Lys Leu Thr Leu Lys Phe Ile Cys Thr Thr Gly Lys Leu Pro
                725                 730                 735

Val Pro Trp Pro Thr Leu Val Thr Thr Leu Thr Tyr Gly Val Gln Cys
            740                 745                 750

Phe Ser Arg Tyr Pro Asp His Met Lys Gln His Asp Phe Phe Lys Ser
            755                 760                 765

Ala Met Pro Glu Gly Tyr Val Gln Glu Arg Thr Ile Phe Phe Lys Asp
770                 775                 780

Asp Gly Asn Tyr Lys Thr Arg Ala Glu Val Lys Phe Glu Gly Asp Thr
785                 790                 795                 800

Leu Val Asn Arg Ile Glu Leu Lys Gly Ile Asp Phe Lys Glu Asp Gly
                805                 810                 815

Asn Ile Leu Gly His Lys Leu Glu Tyr Asn Tyr Asn Ser His Asn Val
            820                 825                 830

Tyr Ile Met Ala Asp Lys Gln Lys Asn Gly Ile Lys Val Asn Phe Lys
            835                 840                 845

Ile Arg His Asn Ile Glu Asp Gly Ser Val Gln Leu Ala Asp His Tyr
850                 855                 860

Gln Gln Asn Thr Pro Ile Gly Asp Gly Pro Val Leu Leu Pro Asp Asn

```
                        865                 870                 875                 880
His Tyr Leu Ser Thr Gln Ser Ala Leu Ser Lys Asp Pro Asn Glu Lys
                885                 890                 895

Arg Asp His Met Val Leu Leu Glu Phe Val Thr Ala Ala Gly Ile Thr
            900                 905                 910

Leu Gly Met Asp Glu Leu Tyr Lys
        915                 920

<210> SEQ ID NO 14
<211> LENGTH: 1002
<212> TYPE: PRT
<213> ORGANISM: artificial sequence
<220> FEATURE:
<223> OTHER INFORMATION: TAT-PKC Beta II GFP fusion protein

<400> SEQUENCE: 14

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Leu Gly Tyr Gly Arg Lys Lys Arg Arg Gln Arg
        35                  40                  45

Arg Arg Gly Gly Ser Thr Met Ser Gly Tyr Pro Tyr Asp Val Pro Asp
    50                  55                  60

Tyr Ala Gly Ser Met Ala Gly Thr Gly Leu Glu Lys Met Ala Asp Pro
65                  70                  75                  80

Ala Ala Met Ala Asp Pro Ala Ala Gly Pro Pro Pro Ser Glu Gly Glu
                85                  90                  95

Glu Ser Thr Val Arg Phe Ala Arg Lys Gly Ala Leu Arg Gln Lys Asn
            100                 105                 110

Val His Glu Val Lys Asn His Lys Phe Thr Ala Arg Phe Phe Lys Gln
        115                 120                 125

Pro Thr Phe Cys Ser His Cys Thr Asp Phe Ile Trp Gly Phe Gly Lys
    130                 135                 140

Gln Gly Phe Gln Cys Gln Val Cys Cys Phe Val Val His Lys Arg Cys
145                 150                 155                 160

His Glu Phe Val Thr Phe Ser Cys Pro Gly Ala Asp Lys Gly Pro Ala
                165                 170                 175

Ser Asp Asp Pro Arg Ser Lys His Lys Phe Lys Ile His Thr Tyr Ser
            180                 185                 190

Ser Pro Thr Phe Cys Asp His Cys Gly Ser Leu Leu Tyr Gly Leu Ile
        195                 200                 205

His Gln Gly Met Lys Cys Asp Thr Cys Met Met Asn Val His Lys Arg
    210                 215                 220

Cys Val Met Asn Val Pro Ser Leu Cys Gly Thr Asp His Thr Glu Arg
225                 230                 235                 240

Arg Gly Arg Ile Tyr Ile Gln Ala His Ile Asp Arg Asp Val Leu Ile
                245                 250                 255

Val Leu Val Arg Asp Ala Lys Asn Leu Val Pro Met Asp Pro Asn Gly
            260                 265                 270

Leu Ser Asp Pro Tyr Val Lys Leu Lys Leu Ile Pro Asp Pro Lys Ser
        275                 280                 285

Glu Ser Lys Gln Lys Thr Lys Thr Ile Lys Cys Ser Leu Asn Pro Glu
    290                 295                 300

Trp Asn Glu Thr Phe Arg Phe Gln Leu Lys Glu Ser Asp Lys Asp Arg
```

```
                305                 310                 315                 320
Arg Leu Ser Val Glu Ile Trp Asp Trp Asp Leu Thr Ser Arg Asn Asp
                    325                 330                 335

Phe Met Gly Ser Leu Ser Phe Gly Ile Ser Glu Leu Gln Lys Ala Ser
                340                 345                 350

Val Asp Gly Trp Phe Lys Leu Leu Ser Gln Glu Glu Gly Glu Tyr Phe
                355                 360                 365

Asn Val Pro Val Pro Pro Glu Gly Ser Glu Ala Asn Glu Glu Leu Arg
370                 375                 380

Gln Lys Phe Glu Arg Ala Lys Ile Ser Gln Gly Thr Lys Val Pro Glu
385                 390                 395                 400

Glu Lys Thr Thr Asn Thr Val Ser Lys Phe Asp Asn Gly Asn Arg
                    405                 410                 415

Asp Arg Met Lys Leu Thr Asp Phe Asn Phe Leu Met Val Leu Gly Lys
                420                 425                 430

Gly Ser Phe Gly Lys Val Met Leu Ser Glu Arg Lys Gly Thr Asp Glu
                435                 440                 445

Leu Tyr Ala Val Lys Ile Leu Lys Lys Asp Val Val Ile Gln Asp Asp
        450                 455                 460

Asp Val Glu Cys Thr Met Val Glu Lys Arg Val Leu Ala Leu Pro Gly
465                 470                 475                 480

Lys Pro Gln Thr Met Asp Arg Leu Tyr Phe Val Met Glu Tyr Val Asn
                485                 490                 495

Gly Gly Asp Leu Met Tyr His Ile Gln Gln Val Gly Arg Phe Lys Glu
                500                 505                 510

Pro His Ala Val Phe Tyr Ala Ala Glu Ile Pro Phe Leu Thr Gln Leu
            515                 520                 525

His Ser Cys Phe Ala Ile Gly Leu Phe Phe Leu Gln Ser Lys Gly Ile
        530                 535                 540

Ile Tyr Arg Asp Leu Lys Leu Asp Asn Val Met Leu Asp Ser Glu Gly
545                 550                 555                 560

His Ile Lys Ile Ala Asp Phe Gly Met Cys Lys Glu Asn Ile Trp Asp
                565                 570                 575

Gly Val Thr Thr Lys Thr Phe Cys Gly Thr Pro Asp Tyr Ile Ala Pro
                580                 585                 590

Glu Ile Ile Ala Tyr Gln Pro Tyr Gly Lys Ser Val Asp Trp Trp Ala
            595                 600                 605

Phe Gly Val Leu Leu Tyr Glu Met Leu Ala Gly Gln Ala Pro Phe Glu
        610                 615                 620

Gly Glu Asp Glu Asp Glu Leu Phe Gln Ser Ile Met Glu His Asn Val
625                 630                 635                 640

Ala Tyr Pro Lys Ser Met Ser Lys Glu Ala Val Ala Ile Cys Lys Gly
                645                 650                 655

Leu Met Thr Lys His Pro Gly Lys Arg Leu Gly Cys Gly Pro Glu Gly
                660                 665                 670

Glu Arg Asp Ile Lys Glu His Ala Phe Phe Arg Tyr Ile Asp Trp Glu
            675                 680                 685

Lys Leu Glu Arg Lys Glu Ile Gln Pro Pro Tyr Lys Pro Lys Ala Cys
        690                 695                 700

Gly Arg Asn Ala Glu Asn Phe Asp Arg Phe Phe Thr Arg His Pro Pro
705                 710                 715                 720

Val Leu Thr Pro Pro Asp Gln Glu Val Ile Arg Asn Ile Asp Gln Ser
                725                 730                 735
```

-continued

```
Glu Phe Glu Gly Phe Ser Phe Val Asn Ser Glu Phe Leu Lys Pro Glu
                740                 745                 750

Val Lys Ser Ala Arg Asp Pro Val Ala Thr Met Val Ser Lys Gly
    755                 760                 765

Glu Glu Leu Phe Thr Gly Val Val Pro Ile Leu Val Glu Leu Asp Gly
770                 775                 780

Asp Val Asn Gly His Lys Phe Ser Val Ser Gly Glu Gly Glu Gly Asp
785                 790                 795                 800

Ala Thr Tyr Gly Lys Leu Thr Leu Lys Phe Ile Cys Thr Thr Gly Lys
                805                 810                 815

Leu Pro Val Pro Trp Pro Thr Leu Val Thr Thr Leu Thr Tyr Gly Val
                820                 825                 830

Gln Cys Phe Ser Arg Tyr Pro Asp His Met Lys Gln His Asp Phe Phe
                835                 840                 845

Lys Ser Ala Met Pro Glu Gly Tyr Val Gln Glu Arg Thr Ile Phe Phe
    850                 855                 860

Lys Asp Asp Gly Asn Tyr Lys Thr Arg Ala Glu Val Lys Phe Glu Gly
865                 870                 875                 880

Asp Thr Leu Val Asn Arg Ile Glu Leu Lys Gly Ile Asp Phe Lys Glu
                885                 890                 895

Asp Gly Asn Ile Leu Gly His Lys Leu Glu Tyr Asn Tyr Asn Ser His
                900                 905                 910

Asn Val Tyr Ile Met Ala Asp Lys Gln Lys Asn Gly Ile Lys Val Asn
                915                 920                 925

Phe Lys Ile Arg His Asn Ile Glu Asp Gly Ser Val Gln Leu Ala Asp
    930                 935                 940

His Tyr Gln Gln Asn Thr Pro Ile Gly Asp Gly Pro Val Leu Leu Pro
945                 950                 955                 960

Asp Asn His Tyr Leu Ser Thr Gln Ser Ala Leu Ser Lys Asp Pro Asn
                965                 970                 975

Glu Lys Arg Asp His Met Val Leu Leu Glu Phe Val Thr Ala Ala Gly
                980                 985                 990

Ile Thr Leu Gly Met Asp Glu Leu Tyr Lys
                995                 1000
```

<210> SEQ ID NO 15
<211> LENGTH: 1002
<212> TYPE: PRT
<213> ORGANISM: artificial sequence
<220> FEATURE:
<223> OTHER INFORMATION: TAT-PKC Beta II GFP A1-2 fusion protein

<400> SEQUENCE: 15

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Lys Leu Gly Tyr Gly Arg Lys Lys Arg Gln Arg
                35                  40                  45

Arg Arg Gly Gly Ser Thr Met Ser Gly Tyr Pro Tyr Asp Val Pro Asp
    50                  55                  60

Tyr Ala Gly Ser Met Ala Gly Thr Gly Leu Glu Lys Met Ala Asp Pro
65                  70                  75                  80

Ala Ala Met Ala Asp Pro Ala Ala Gly Pro Pro Ser Glu Gly Glu
                85                  90                  95
```

```
Glu Ser Thr Val Arg Phe Ala Arg Lys Ile Tyr Leu Arg Pro Lys Asn
            100                 105                 110

Val His Glu Val Lys Asn His Lys Phe Thr Ala Arg Phe Phe Lys Gln
            115                 120                 125

Pro Thr Phe Cys Ser His Cys Thr Asp Phe Ile Trp Gly Phe Gly Lys
        130                 135                 140

Gln Gly Phe Gln Cys Gln Val Cys Cys Phe Val Val His Lys Arg Cys
145                 150                 155                 160

His Glu Phe Val Thr Phe Ser Cys Pro Gly Ala Asp Lys Gly Pro Ala
                165                 170                 175

Ser Asp Asp Pro Arg Ser Lys His Lys Phe Lys Ile His Thr Tyr Ser
                180                 185                 190

Ser Pro Thr Phe Cys Asp His Cys Gly Ser Leu Leu Tyr Gly Leu Ile
                195                 200                 205

His Gln Gly Met Lys Cys Asp Thr Cys Met Met Asn Val His Lys Arg
        210                 215                 220

Cys Val Met Asn Val Pro Ser Leu Cys Gly Thr Asp His Thr Glu Arg
225                 230                 235                 240

Arg Gly Arg Ile Tyr Ile Gln Ala His Ile Asp Arg Asp Val Leu Ile
                245                 250                 255

Val Leu Val Arg Asp Ala Lys Asn Leu Val Pro Met Asp Pro Asn Gly
                260                 265                 270

Leu Ser Asp Pro Tyr Val Lys Leu Lys Leu Ile Pro Asp Pro Lys Ser
        275                 280                 285

Glu Ser Lys Gln Lys Thr Lys Thr Ile Lys Cys Ser Leu Asn Pro Glu
        290                 295                 300

Trp Asn Glu Thr Phe Arg Phe Gln Leu Lys Glu Ser Asp Lys Asp Arg
305                 310                 315                 320

Arg Leu Ser Val Glu Ile Trp Asp Trp Asp Leu Thr Ser Arg Asn Asp
                325                 330                 335

Phe Met Gly Ser Leu Ser Phe Gly Ile Ser Glu Leu Gln Lys Ala Ser
        340                 345                 350

Val Asp Gly Trp Phe Lys Leu Leu Ser Gln Glu Glu Gly Glu Tyr Phe
        355                 360                 365

Asn Val Pro Val Pro Pro Glu Gly Ser Glu Ala Asn Glu Glu Leu Arg
        370                 375                 380

Gln Lys Phe Glu Arg Ala Lys Ile Ser Gln Gly Thr Lys Val Pro Glu
385                 390                 395                 400

Glu Lys Thr Thr Asn Thr Val Ser Lys Phe Asp Asn Asn Gly Asn Arg
                405                 410                 415

Asp Arg Met Lys Leu Thr Asp Phe Asn Phe Leu Met Val Leu Gly Lys
                420                 425                 430

Gly Ser Phe Gly Lys Val Met Leu Ser Glu Arg Lys Gly Thr Asp Glu
        435                 440                 445

Leu Tyr Ala Val Lys Ile Leu Lys Lys Asp Val Val Ile Gln Asp Asp
        450                 455                 460

Asp Val Glu Cys Thr Met Val Glu Lys Arg Val Leu Ala Leu Pro Gly
465                 470                 475                 480

Lys Pro Gln Thr Met Asp Arg Leu Tyr Phe Val Met Glu Tyr Val Asn
                485                 490                 495

Gly Gly Asp Leu Met Tyr His Ile Gln Gln Val Gly Arg Phe Lys Glu
        500                 505                 510
```

-continued

```
Pro His Ala Val Phe Tyr Ala Ala Glu Ile Pro Phe Leu Thr Gln Leu
        515                 520                 525
His Ser Cys Phe Ala Ile Gly Leu Phe Phe Leu Gln Ser Lys Gly Ile
        530                 535                 540
Ile Tyr Arg Asp Leu Lys Leu Asp Asn Val Met Leu Asp Ser Glu Gly
545                 550                 555                 560
His Ile Lys Ile Ala Asp Phe Gly Met Cys Lys Glu Asn Ile Trp Asp
                565                 570                 575
Gly Val Thr Thr Lys Thr Phe Cys Gly Thr Pro Asp Tyr Ile Ala Pro
            580                 585                 590
Glu Ile Ile Ala Tyr Gln Pro Tyr Gly Lys Ser Val Asp Trp Trp Ala
        595                 600                 605
Phe Gly Val Leu Leu Tyr Glu Met Leu Ala Gly Gln Ala Pro Phe Glu
    610                 615                 620
Gly Glu Asp Glu Asp Glu Leu Phe Gln Ser Ile Met Glu His Asn Val
625                 630                 635                 640
Ala Tyr Pro Lys Ser Met Ser Lys Glu Ala Val Ala Ile Cys Lys Gly
                645                 650                 655
Leu Met Thr Lys His Pro Gly Lys Arg Leu Gly Cys Gly Pro Glu Gly
            660                 665                 670
Glu Arg Asp Ile Lys Glu His Ala Phe Phe Arg Tyr Ile Asp Trp Glu
        675                 680                 685
Lys Leu Glu Arg Lys Glu Ile Gln Pro Pro Tyr Lys Pro Lys Ala Cys
    690                 695                 700
Gly Arg Asn Ala Glu Asn Phe Asp Arg Phe Phe Thr Arg His Pro Pro
705                 710                 715                 720
Val Leu Thr Pro Pro Asp Gln Glu Val Ile Arg Asn Ile Asp Gln Ser
                725                 730                 735
Glu Phe Glu Gly Phe Ser Phe Val Asn Ser Glu Phe Leu Lys Pro Glu
            740                 745                 750
Val Lys Ser Ala Arg Asp Pro Val Ala Thr Met Val Ser Lys Gly
        755                 760                 765
Glu Glu Leu Phe Thr Gly Val Val Pro Ile Leu Val Glu Leu Asp Gly
    770                 775                 780
Asp Val Asn Gly His Lys Phe Ser Val Ser Gly Glu Gly Glu Gly Asp
785                 790                 795                 800
Ala Thr Tyr Gly Lys Leu Thr Leu Lys Phe Ile Cys Thr Thr Gly Lys
                805                 810                 815
Leu Pro Val Pro Trp Pro Thr Leu Val Thr Thr Leu Thr Tyr Gly Val
            820                 825                 830
Gln Cys Phe Ser Arg Tyr Pro Asp His Met Lys Gln His Asp Phe Phe
        835                 840                 845
Lys Ser Ala Met Pro Glu Gly Tyr Val Gln Glu Arg Thr Ile Phe Phe
    850                 855                 860
Lys Asp Asp Gly Asn Tyr Lys Thr Arg Ala Glu Val Lys Phe Glu Gly
865                 870                 875                 880
Asp Thr Leu Val Asn Arg Ile Glu Leu Lys Gly Ile Asp Phe Lys Glu
                885                 890                 895
Asp Gly Asn Ile Leu Gly His Lys Leu Glu Tyr Asn Tyr Asn Ser His
            900                 905                 910
Asn Val Tyr Ile Met Ala Asp Lys Gln Lys Asn Gly Ile Lys Val Asn
        915                 920                 925
Phe Lys Ile Arg His Asn Ile Glu Asp Gly Ser Val Gln Leu Ala Asp
```

```
                930             935             940
His Tyr Gln Gln Asn Thr Pro Ile Gly Asp Gly Pro Val Leu Leu Pro
945                 950             955                 960

Asp Asn His Tyr Leu Ser Thr Gln Ser Ala Leu Ser Lys Asp Pro Asn
                965             970             975

Glu Lys Arg Asp His Met Val Leu Leu Glu Phe Val Thr Ala Ala Gly
            980             985             990

Ile Thr Leu Gly Met Asp Glu Leu Tyr Lys
        995             1000
```

<210> SEQ ID NO 16
<211> LENGTH: 1002
<212> TYPE: PRT
<213> ORGANISM: artificial sequence
<220> FEATURE:
<223> OTHER INFORMATION: TAT-PKC Beta II GFP A2-1 fusion protein

<400> SEQUENCE: 16

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Lys Leu Gly Tyr Gly Arg Lys Lys Arg Gln Arg
            35                  40                  45

Arg Arg Gly Gly Ser Thr Met Ser Gly Tyr Pro Tyr Asp Val Pro Asp
50                  55                  60

Tyr Ala Gly Ser Met Ala Gly Thr Gly Leu Glu Lys Met Ala Asp Pro
65                  70                  75                  80

Ala Ala Met Ala Asp Pro Ala Ala Gly Pro Pro Pro Ser Glu Gly Glu
                85                  90                  95

Glu Ser Thr Val Arg Phe Ala Arg Lys Ile Tyr Leu Arg Phe Lys Asn
                100                 105                 110

Val His Glu Val Lys Asn His Lys Phe Thr Ala Arg Phe Phe Lys Gln
                115                 120                 125

Pro Thr Phe Cys Ser His Cys Thr Asp Phe Ile Trp Gly Phe Gly Lys
                130                 135                 140

Gln Gly Phe Gln Cys Gln Val Cys Cys Phe Val Val His Lys Arg Cys
145                 150                 155                 160

His Glu Phe Val Thr Phe Ser Cys Pro Gly Ala Asp Lys Gly Pro Ala
                165                 170                 175

Ser Asp Asp Pro Arg Ser Lys His Lys Phe Lys Ile His Thr Tyr Ser
                180                 185                 190

Ser Pro Thr Phe Cys Asp His Cys Gly Ser Leu Leu Tyr Gly Leu Ile
                195                 200                 205

His Gln Gly Met Lys Cys Asp Thr Cys Met Met Asn Val His Lys Arg
                210                 215                 220

Cys Val Met Asn Val Pro Ser Leu Cys Gly Thr Asp His Thr Glu Arg
225                 230                 235                 240

Arg Gly Arg Ile Tyr Ile Gln Ala His Ile Asp Arg Asp Val Leu Ile
                245                 250                 255

Val Leu Val Arg Asp Ala Lys Asn Leu Val Pro Met Asp Pro Asn Gly
                260                 265                 270

Leu Ser Asp Pro Tyr Val Lys Leu Lys Leu Ile Pro Asp Pro Lys Ser
                275                 280                 285

Glu Ser Lys Gln Lys Thr Lys Thr Ile Lys Cys Ser Leu Asn Pro Glu
```

```
            290                 295                 300
Trp Asn Glu Thr Phe Arg Phe Gln Leu Lys Glu Ser Asp Lys Asp Arg
305                 310                 315                 320

Arg Leu Ser Val Glu Ile Trp Asp Trp Asp Leu Thr Ser Arg Asn Asp
                325                 330                 335

Phe Met Gly Ser Leu Ser Phe Gly Ile Ser Glu Leu Gln Lys Ala Ser
                340                 345                 350

Val Asp Gly Trp Phe Lys Leu Leu Ser Gln Glu Glu Gly Glu Tyr Phe
                355                 360                 365

Asn Val Pro Val Pro Glu Gly Ser Glu Ala Asn Glu Glu Leu Arg
370                 375                 380

Gln Lys Phe Glu Arg Ala Lys Ile Ser Gln Gly Thr Lys Val Pro Glu
385                 390                 395                 400

Glu Lys Thr Thr Asn Thr Val Ser Lys Phe Asp Asn Asn Gly Asn Arg
                405                 410                 415

Asp Arg Met Lys Leu Thr Asp Phe Asn Phe Leu Met Val Leu Gly Lys
                420                 425                 430

Gly Ser Phe Gly Lys Val Met Leu Ser Glu Arg Lys Gly Thr Asp Glu
                435                 440                 445

Leu Tyr Ala Val Lys Ile Leu Lys Lys Asp Val Val Ile Gln Asp Asp
                450                 455                 460

Asp Val Glu Cys Thr Met Val Glu Lys Arg Val Leu Ala Leu Pro Gly
465                 470                 475                 480

Lys Pro Gln Thr Met Asp Arg Leu Tyr Phe Val Met Glu Tyr Val Asn
                485                 490                 495

Gly Gly Asp Leu Met Tyr His Ile Gln Gln Val Gly Arg Phe Lys Glu
                500                 505                 510

Pro His Ala Val Phe Tyr Ala Ala Glu Ile Pro Phe Leu Thr Gln Leu
                515                 520                 525

His Ser Cys Phe Ala Ile Gly Leu Phe Phe Leu Gln Ser Lys Gly Ile
                530                 535                 540

Ile Tyr Arg Asp Leu Lys Leu Asp Asn Val Met Leu Asp Ser Glu Gly
545                 550                 555                 560

His Ile Lys Ile Ala Asp Phe Gly Met Cys Lys Glu Asn Ile Trp Asp
                565                 570                 575

Gly Val Thr Thr Lys Thr Phe Cys Gly Thr Pro Asp Tyr Ile Ala Pro
                580                 585                 590

Glu Ile Ile Ala Tyr Gln Pro Tyr Gly Lys Ser Val Asp Trp Trp Ala
                595                 600                 605

Phe Gly Val Leu Leu Tyr Glu Met Leu Ala Gly Gln Ala Pro Phe Glu
610                 615                 620

Gly Glu Asp Glu Asp Leu Phe Gln Ser Ile Met Glu His Asn Val
625                 630                 635                 640

Ala Tyr Pro Lys Ser Met Ser Lys Glu Ala Val Ala Ile Cys Lys Gly
                645                 650                 655

Leu Met Thr Lys His Pro Gly Lys Arg Leu Gly Cys Gly Pro Glu Gly
                660                 665                 670

Glu Arg Asp Ile Lys Glu His Ala Phe Phe Arg Tyr Ile Asp Trp Glu
                675                 680                 685

Lys Leu Glu Arg Lys Glu Ile Gln Pro Pro Tyr Lys Pro Lys Ala Cys
                690                 695                 700

Gly Arg Asn Ala Glu Asn Phe Asp Arg Phe Phe Thr Arg His Pro Pro
705                 710                 715                 720
```

```
Val Leu Thr Pro Pro Asp Gln Glu Val Ile Arg Asn Ile Asp Gln Ser
            725                 730                 735

Glu Phe Glu Gly Phe Ser Phe Val Asn Ser Glu Phe Leu Lys Pro Glu
            740                 745                 750

Val Lys Ser Ala Arg Asp Pro Pro Val Ala Thr Met Val Ser Lys Gly
            755                 760                 765

Glu Glu Leu Phe Thr Gly Val Val Pro Ile Leu Val Glu Leu Asp Gly
            770                 775                 780

Asp Val Asn Gly His Lys Phe Ser Val Ser Gly Glu Gly Glu Gly Asp
785                 790                 795                 800

Ala Thr Tyr Gly Lys Leu Thr Leu Lys Phe Ile Cys Thr Thr Gly Lys
            805                 810                 815

Leu Pro Val Pro Trp Pro Thr Leu Val Thr Thr Leu Thr Tyr Gly Val
            820                 825                 830

Gln Cys Phe Ser Arg Tyr Pro Asp His Met Lys Gln His Asp Phe Phe
            835                 840                 845

Lys Ser Ala Met Pro Glu Gly Tyr Val Gln Glu Arg Thr Ile Phe Phe
            850                 855                 860

Lys Asp Asp Gly Asn Tyr Lys Thr Arg Ala Glu Val Lys Phe Glu Gly
865                 870                 875                 880

Asp Thr Leu Val Asn Arg Ile Glu Leu Lys Gly Ile Asp Phe Lys Glu
            885                 890                 895

Asp Gly Asn Ile Leu Gly His Lys Leu Glu Tyr Asn Tyr Asn Ser His
            900                 905                 910

Asn Val Tyr Ile Met Ala Asp Lys Gln Lys Asn Gly Ile Lys Val Asn
            915                 920                 925

Phe Lys Ile Arg His Asn Ile Glu Asp Gly Ser Val Gln Leu Ala Asp
            930                 935                 940

His Tyr Gln Gln Asn Thr Pro Ile Gly Asp Gly Pro Val Leu Leu Pro
945                 950                 955                 960

Asp Asn His Tyr Leu Ser Thr Gln Ser Ala Leu Ser Lys Asp Pro Asn
            965                 970                 975

Glu Lys Arg Asp His Met Val Leu Leu Glu Phe Val Thr Ala Ala Gly
            980                 985                 990

Ile Thr Leu Gly Met Asp Glu Leu  Tyr Lys
            995                 1000

<210> SEQ ID NO 17
<211> LENGTH: 1002
<212> TYPE: PRT
<213> ORGANISM: artificial sequence
<220> FEATURE:
<223> OTHER INFORMATION: TAT-PKC Beta II GFP A3-4 fusion protein

<400> SEQUENCE: 17

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Lys Leu Gly Tyr Gly Arg Lys Lys Arg Arg Gln Arg
            35                  40                  45

Arg Arg Gly Gly Ser Thr Met Ser Gly Tyr Pro Tyr Asp Val Pro Asp
50                  55                  60

Tyr Ala Gly Ser Met Ala Gly Thr Gly Leu Glu Lys Met Ala Asp Pro
65                  70                  75                  80
```

-continued

Ala Ala Met Ala Asp Pro Ala Ala Gly Pro Pro Ser Glu Gly Glu
            85                  90              95

Glu Ser Thr Val Arg Phe Ala Arg Lys Ile Tyr Leu Arg Thr Lys Asn
                100                 105                 110

Val His Glu Val Lys Asn His Lys Phe Thr Ala Arg Phe Phe Lys Gln
        115                 120                 125

Pro Thr Phe Cys Ser His Cys Thr Asp Phe Ile Trp Gly Phe Gly Lys
    130                 135                 140

Gln Gly Phe Gln Cys Gln Val Cys Cys Phe Val Val His Lys Arg Cys
145                 150                 155                 160

His Glu Phe Val Thr Phe Ser Cys Pro Gly Ala Asp Lys Gly Pro Ala
                165                 170                 175

Ser Asp Asp Pro Arg Ser Lys His Lys Phe Lys Ile His Thr Tyr Ser
                180                 185                 190

Ser Pro Thr Phe Cys Asp His Cys Gly Ser Leu Leu Tyr Gly Leu Ile
            195                 200                 205

His Gln Gly Met Lys Cys Asp Thr Cys Met Met Asn Val His Lys Arg
    210                 215                 220

Cys Val Met Asn Val Pro Ser Leu Cys Gly Thr Asp His Thr Glu Arg
225                 230                 235                 240

Arg Gly Arg Ile Tyr Ile Gln Ala His Ile Asp Arg Asp Val Leu Ile
                245                 250                 255

Val Leu Val Arg Asp Ala Lys Asn Leu Val Pro Met Asp Pro Asn Gly
                260                 265                 270

Leu Ser Asp Pro Tyr Val Lys Leu Lys Leu Ile Pro Asp Pro Lys Ser
            275                 280                 285

Glu Ser Lys Gln Lys Thr Lys Thr Ile Lys Cys Ser Leu Asn Pro Glu
    290                 295                 300

Trp Asn Glu Thr Phe Arg Phe Gln Leu Lys Glu Ser Asp Lys Asp Arg
305                 310                 315                 320

Arg Leu Ser Val Glu Ile Trp Asp Trp Asp Leu Thr Ser Arg Asn Asp
                325                 330                 335

Phe Met Gly Ser Leu Ser Phe Gly Ile Ser Glu Leu Gln Lys Ala Ser
                340                 345                 350

Val Asp Gly Trp Phe Lys Leu Leu Ser Gln Glu Glu Gly Glu Tyr Phe
            355                 360                 365

Asn Val Pro Val Pro Pro Glu Gly Ser Glu Ala Asn Glu Glu Leu Arg
    370                 375                 380

Gln Lys Phe Glu Arg Ala Lys Ile Ser Gln Gly Thr Lys Val Pro Glu
385                 390                 395                 400

Glu Lys Thr Thr Asn Thr Val Ser Lys Phe Asp Asn Asn Gly Asn Arg
                405                 410                 415

Asp Arg Met Lys Leu Thr Asp Phe Asn Phe Leu Met Val Leu Gly Lys
                420                 425                 430

Gly Ser Phe Gly Lys Val Met Leu Ser Glu Arg Lys Gly Thr Asp Glu
            435                 440                 445

Leu Tyr Ala Val Lys Ile Leu Lys Lys Asp Val Val Ile Gln Asp Asp
    450                 455                 460

Asp Val Glu Cys Thr Met Val Glu Lys Arg Val Leu Ala Leu Pro Gly
465                 470                 475                 480

Lys Pro Gln Thr Met Asp Arg Leu Tyr Phe Val Met Glu Tyr Val Asn
                485                 490                 495

-continued

```
Gly Gly Asp Leu Met Tyr His Ile Gln Gln Val Gly Arg Phe Lys Glu
            500                 505                 510
Pro His Ala Val Phe Tyr Ala Ala Glu Ile Pro Phe Leu Thr Gln Leu
        515                 520                 525
His Ser Cys Phe Ala Ile Gly Leu Phe Phe Leu Gln Ser Lys Gly Ile
    530                 535                 540
Ile Tyr Arg Asp Leu Lys Leu Asp Asn Val Met Leu Asp Ser Glu Gly
545                 550                 555                 560
His Ile Lys Ile Ala Asp Phe Gly Met Cys Lys Glu Asn Ile Trp Asp
                565                 570                 575
Gly Val Thr Thr Lys Thr Phe Cys Gly Thr Pro Asp Tyr Ile Ala Pro
            580                 585                 590
Glu Ile Ile Ala Tyr Gln Pro Tyr Gly Lys Ser Val Asp Trp Trp Ala
        595                 600                 605
Phe Gly Val Leu Leu Tyr Glu Met Leu Ala Gly Gln Ala Pro Phe Glu
    610                 615                 620
Gly Glu Asp Glu Asp Glu Leu Phe Gln Ser Ile Met Glu His Asn Val
625                 630                 635                 640
Ala Tyr Pro Lys Ser Met Ser Lys Glu Ala Val Ala Ile Cys Lys Gly
                645                 650                 655
Leu Met Thr Lys His Pro Gly Lys Arg Leu Gly Cys Gly Pro Glu Gly
            660                 665                 670
Glu Arg Asp Ile Lys Glu His Ala Phe Phe Arg Tyr Ile Asp Trp Glu
        675                 680                 685
Lys Leu Glu Arg Lys Glu Ile Gln Pro Pro Tyr Lys Pro Lys Ala Cys
    690                 695                 700
Gly Arg Asn Ala Glu Asn Phe Asp Arg Phe Phe Thr Arg His Pro Pro
705                 710                 715                 720
Val Leu Thr Pro Pro Asp Gln Glu Val Ile Arg Asn Ile Asp Gln Ser
                725                 730                 735
Glu Phe Glu Gly Phe Ser Phe Val Asn Ser Glu Phe Leu Lys Pro Glu
            740                 745                 750
Val Lys Ser Ala Arg Asp Pro Pro Val Ala Thr Met Val Ser Lys Gly
        755                 760                 765
Glu Glu Leu Phe Thr Gly Val Val Pro Ile Leu Val Glu Leu Asp Gly
    770                 775                 780
Asp Val Asn Gly His Lys Phe Ser Val Ser Gly Glu Gly Glu Gly Asp
785                 790                 795                 800
Ala Thr Tyr Gly Lys Leu Thr Leu Lys Phe Ile Cys Thr Thr Gly Lys
                805                 810                 815
Leu Pro Val Pro Trp Pro Thr Leu Val Thr Thr Leu Thr Tyr Gly Val
            820                 825                 830
Gln Cys Phe Ser Arg Tyr Pro Asp His Met Lys Gln His Asp Phe Phe
        835                 840                 845
Lys Ser Ala Met Pro Glu Gly Tyr Val Gln Glu Arg Thr Ile Phe Phe
    850                 855                 860
Lys Asp Asp Gly Asn Tyr Lys Thr Arg Ala Glu Val Lys Phe Glu Gly
865                 870                 875                 880
Asp Thr Leu Val Asn Arg Ile Glu Leu Lys Gly Ile Asp Phe Lys Glu
                885                 890                 895
Asp Gly Asn Ile Leu Gly His Lys Leu Glu Tyr Asn Tyr Asn Ser His
            900                 905                 910
Asn Val Tyr Ile Met Ala Asp Lys Gln Lys Asn Gly Ile Lys Val Asn
```

```
                    915                 920                 925
Phe Lys Ile Arg His Asn Ile Glu Asp Gly Ser Val Gln Leu Ala Asp
        930                 935                 940

His Tyr Gln Gln Asn Thr Pro Ile Gly Asp Gly Pro Val Leu Leu Pro
945                 950                 955                 960

Asp Asn His Tyr Leu Ser Thr Gln Ser Ala Leu Ser Lys Asp Pro Asn
                965                 970                 975

Glu Lys Arg Asp His Met Val Leu Leu Glu Phe Val Thr Ala Ala Gly
            980                 985                 990

Ile Thr Leu Gly Met Asp Glu Leu  Tyr Lys
            995                 1000

<210> SEQ ID NO 18
<211> LENGTH: 1002
<212> TYPE: PRT
<213> ORGANISM: artificial sequence
<220> FEATURE:
<223> OTHER INFORMATION: TAT-PKC Beta II GFP A4-6 fusion protein

<400> SEQUENCE: 18

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Lys Leu Gly Tyr Gly Arg Lys Lys Arg Gln Arg
            35                  40                  45

Arg Arg Gly Gly Ser Thr Met Ser Gly Tyr Pro Tyr Asp Val Pro Asp
50                  55                  60

Tyr Ala Gly Ser Met Ala Gly Thr Gly Leu Glu Lys Met Ala Asp Pro
65                  70                  75                  80

Ala Ala Met Ala Asp Pro Ala Ala Gly Pro Pro Ser Glu Gly Glu
                85                  90                  95

Glu Ser Thr Val Arg Phe Ala Arg Lys Ser Tyr Leu Arg Phe Lys Asn
                100                 105                 110

Val His Glu Val Lys Asn His Lys Phe Thr Ala Arg Phe Phe Lys Gln
                115                 120                 125

Pro Thr Phe Cys Ser His Cys Thr Asp Phe Ile Trp Gly Phe Gly Lys
        130                 135                 140

Gln Gly Phe Gln Cys Gln Val Cys Cys Phe Val Val His Lys Arg Cys
145                 150                 155                 160

His Glu Pro Val Thr Phe Ser Cys Pro Gly Ala Asp Lys Gly Pro Ala
                165                 170                 175

Ser Asp Asp Pro Arg Ser Lys His Lys Phe Lys Ile His Thr Tyr Ser
                180                 185                 190

Ser Pro Thr Phe Cys Asp His Cys Gly Ser Leu Leu Tyr Gly Leu Ile
        195                 200                 205

His Gln Gly Met Lys Cys Asp Thr Cys Met Met Asn Val His Lys Arg
        210                 215                 220

Cys Val Met Asn Val Pro Ser Leu Cys Gly Thr Asp His Thr Glu Arg
225                 230                 235                 240

Arg Gly Arg Ile Tyr Ile Gln Ala His Ile Asp Arg Asp Val Leu Ile
                245                 250                 255

Val Leu Val Arg Asp Ala Lys Asn Leu Val Pro Met Asp Pro Asn Gly
                260                 265                 270

Leu Ser Asp Pro Tyr Val Lys Leu Lys Leu Ile Pro Asp Pro Lys Ser
```

|       |       |       |       | 275   |       |       |       | 280   |       |       |       | 285   |       |       |       |
|-------|-------|-------|-------|-------|-------|-------|-------|-------|-------|-------|-------|-------|-------|-------|-------|

Glu Ser Lys Gln Lys Thr Lys Thr Ile Lys Cys Ser Leu Asn Pro Glu
290                 295                 300

Trp Asn Glu Thr Phe Arg Phe Gln Leu Lys Glu Ser Asp Lys Asp Arg
305                 310                 315                 320

Arg Leu Ser Val Glu Ile Trp Asp Trp Asp Leu Thr Ser Arg Asn Asp
                    325                 330                 335

Phe Met Gly Ser Leu Ser Phe Gly Ile Ser Glu Leu Gln Lys Ala Ser
                340                 345                 350

Val Asp Gly Trp Phe Lys Leu Leu Ser Gln Glu Glu Gly Glu Tyr Phe
            355                 360                 365

Asn Val Pro Val Pro Pro Glu Gly Ser Glu Ala Asn Glu Glu Leu Arg
        370                 375                 380

Gln Lys Phe Glu Arg Ala Lys Ile Ser Gln Gly Thr Lys Val Pro Glu
385                 390                 395                 400

Glu Lys Thr Thr Asn Thr Val Ser Lys Phe Asp Asn Asn Gly Asn Arg
                    405                 410                 415

Asp Arg Met Lys Leu Thr Asp Phe Asn Phe Leu Met Val Leu Gly Lys
                420                 425                 430

Gly Ser Phe Gly Lys Val Met Leu Ser Glu Arg Lys Gly Thr Asp Glu
            435                 440                 445

Leu Tyr Ala Val Lys Ile Leu Lys Lys Asp Val Val Ile Gln Asp Asp
        450                 455                 460

Asp Val Glu Cys Thr Met Val Glu Lys Arg Val Leu Ala Leu Pro Gly
465                 470                 475                 480

Lys Pro Gln Thr Met Asp Arg Leu Tyr Phe Val Met Glu Tyr Val Asn
                    485                 490                 495

Gly Gly Asp Leu Met Tyr His Ile Gln Gln Val Gly Arg Phe Lys Glu
                500                 505                 510

Pro His Ala Val Phe Tyr Ala Ala Glu Ile Pro Phe Leu Thr Gln Leu
            515                 520                 525

His Ser Cys Phe Ala Ile Gly Leu Phe Phe Leu Gln Ser Lys Gly Ile
        530                 535                 540

Ile Tyr Arg Asp Leu Lys Leu Asp Asn Val Met Leu Asp Ser Glu Gly
545                 550                 555                 560

His Ile Lys Ile Ala Asp Phe Gly Met Cys Lys Glu Asn Ile Trp Asp
                    565                 570                 575

Gly Val Thr Thr Lys Thr Phe Cys Gly Thr Pro Asp Tyr Ile Ala Pro
                580                 585                 590

Glu Ile Ile Ala Tyr Gln Pro Tyr Gly Lys Ser Val Asp Trp Trp Ala
            595                 600                 605

Phe Gly Val Leu Leu Tyr Glu Met Leu Ala Gly Gln Ala Pro Phe Glu
        610                 615                 620

Gly Glu Asp Glu Asp Glu Leu Phe Gln Ser Ile Met Glu His Asn Val
625                 630                 635                 640

Ala Tyr Pro Lys Ser Met Ser Lys Glu Ala Val Ala Ile Cys Lys Gly
                    645                 650                 655

Leu Met Thr Lys His Pro Gly Lys Arg Leu Gly Cys Gly Pro Glu Gly
                660                 665                 670

Glu Arg Asp Ile Lys Glu His Ala Phe Phe Arg Tyr Ile Asp Trp Glu
            675                 680                 685

Lys Leu Glu Arg Lys Glu Ile Gln Pro Pro Tyr Lys Pro Lys Ala Cys
        690                 695                 700

-continued

```
Gly Arg Asn Ala Glu Asn Phe Asp Arg Phe Phe Thr Arg His Pro Pro
705                 710                 715                 720

Val Leu Thr Pro Pro Asp Gln Glu Val Ile Arg Asn Ile Asp Gln Ser
            725                 730                 735

Glu Phe Glu Gly Phe Ser Phe Val Asn Ser Glu Phe Leu Lys Pro Glu
            740                 745                 750

Val Lys Ser Ala Arg Asp Pro Pro Val Ala Thr Met Val Ser Lys Gly
        755                 760                 765

Glu Glu Leu Phe Thr Gly Val Val Pro Ile Leu Val Glu Leu Asp Gly
        770                 775                 780

Asp Val Asn Gly His Lys Phe Ser Val Ser Gly Glu Gly Glu Gly Asp
785                 790                 795                 800

Ala Thr Tyr Gly Lys Leu Thr Leu Lys Phe Ile Cys Thr Thr Gly Lys
            805                 810                 815

Leu Pro Val Pro Trp Pro Thr Leu Val Thr Thr Leu Thr Tyr Gly Val
            820                 825                 830

Gln Cys Phe Ser Arg Tyr Pro Asp His Met Lys Gln His Asp Phe Phe
            835                 840                 845

Lys Ser Ala Met Pro Glu Gly Tyr Val Gln Glu Arg Thr Ile Phe Phe
850                 855                 860

Lys Asp Asp Gly Asn Tyr Lys Thr Arg Ala Glu Val Lys Phe Glu Gly
865                 870                 875                 880

Asp Thr Leu Val Asn Arg Ile Glu Leu Lys Gly Ile Asp Phe Lys Glu
                885                 890                 895

Asp Gly Asn Ile Leu Gly His Lys Leu Glu Tyr Asn Tyr Asn Ser His
            900                 905                 910

Asn Val Tyr Ile Met Ala Asp Lys Gln Lys Asn Gly Ile Lys Val Asn
            915                 920                 925

Phe Lys Ile Arg His Asn Ile Glu Asp Gly Ser Val Gln Leu Ala Asp
        930                 935                 940

His Tyr Gln Gln Asn Thr Pro Ile Gly Asp Gly Pro Val Leu Leu Pro
945                 950                 955                 960

Asp Asn His Tyr Leu Ser Thr Gln Ser Ala Leu Ser Lys Asp Pro Asn
            965                 970                 975

Glu Lys Arg Asp His Met Val Leu Leu Glu Phe Val Thr Ala Ala Gly
            980                 985                 990

Ile Thr Leu Gly Met Asp Glu Leu  Tyr Lys
        995                 1000
```

PRODRUG ANTI-CANCER THERAPY

CROSS-REFERENCE TO RELATED APPLICATIONS

This application is a continuation application of U.S. application Ser. No. 12/820,827, filed Jun. 22, 2010, and claims priority to U.S. provisional application No. 61/219,220, filed Jun. 22, 2009, the disclosures of each of which are incorporated herein by reference.

FIELD OF THE INVENTION

The present invention relates generally to cancer therapy and more particularly to the design and use of prodrugs to inhibit the growth of cancer cells.

DISCUSSION OF RELATED ART

Cancer continues to be a significant cause of death in humans throughout the world. The search for cancer therapies is complicated by the focus of pharmaceutical interventions on inhibition of signal transduction pathways that are involved in the pro-survival/anti-differentiation aspect of cancer cells. A prototypical example of such a strategy is inhibition of the activity of the fusion oncogene Bcr-Abl, which is expressed in both chronic myelogenous leukemia (CLL) and acute lympohocytic leukemia (ALL). Bcr-Abl has unregulated kinase activity, which is essential form all CML basts to survive and proliferate. The kinase inhibitor sold under the brand GLEEVAC (imatinib) is an Abl-specific inhibitor and is now the standard of care for all phases of CML. Further, imatinib has become the paradigm for inhibiting oncogenic signal transduction as a means of altering leukemic blast (and other transformed cell) biology. However, studies of imatinib-resistant CML have shown that amplification of the bcr-abl gene or mutations in the kinase domain of Bcr-Abl are major mechanisms of drug resistance—demonstrating that CML blasts do not become Bcr-Abl "independent" and underscoring the importance of continued oncogenic signaling for leukemia survival. However, many other cancers, including Bcr-Abl+ALL, have abnormal oncogenic signaling, yet inhibiting this pathway does not necessarily affect the cancer cells because they do not need the signaling pathway for survival. Thus, there is an ongoing need for therapeutic cancer interventions that can exploit endogenous cancer cell specific genes without reliance on inhibiting the function of such genes.

SUMMARY OF THE INVENTION

The present invention provides compositions and methods for inhibiting the growth of cancer cells in an individual. The invention is particularly suited for inhibiting the growth of cancer cells that have constitutively active Abl tyrosine kinase activity, such as Chronic myeloid leukemia (CML) cells, which harbor a:t(9;22)(q34;q11) translocation. This chromosomal rearrangement results in a bcr-abl fusion gene. A chimeric Bcr-Abl protein which has constitutively active Abl tyrosine kinase activity that is believed to play an important role in leukemogenesis is expressed from the bcr-abl fusion gene. Thus, in one embodiment, the invention provides a method for inhibiting growth of cancer cells in an individual, wherein the cancer cells have constitutively active Abl tyrosine kinase activity. The method comprises administering to the individual a modified protein kinase C (PKC) which comprises an Abl tyrosine kinase target motif. It is believed that the modified PKC is phosphorylated by a Bcr-Abl protein expressed by the cancer cells, which results in inhibition of growth of the cells.

The modified PKC is in one embodiment human PKC βII which has been modified to express an Abl tyrosine kinase target motif that comprises the sequence of SEQ ID NO:6. The modified PKC βII can also comprise a cellular transduction domain, such as the HIV-TAT cellular transduction domain. In one embodiment, the cellular transduction domain comprises SEQ ID NO:7.

The method of the invention is particularly suited for providing a therapeutic benefit to an individual who is diagnosed with, suspected of having, or at risk for developing leukemia. In one embodiment, the leukemia is CML. In another embodiment, the leukemia is acute lympohocytic leukemia (ALL).

The invention also comprises a composition comprising a modified protein kinase C (PKC) βII, wherein the modified PCKβII comprises an Abl tyrosine kinase target motif. In one embodiment, the Abl tyrosine kinase target motif comprises the sequence of SEQ ID NO:6. As with the method of the invention, the composition can comprise a modified PKC βII that contains a cellular transduction domain. In one embodiment, the cellular transduction domain comprises SEQ ID NO:7.

The invention also includes a modified PKCβII that is present in a cancer cell which has constitutively active Abl tyrosine kinase activity, and wherein the modified PKCβII is phosphorylated on a Tyr present in the Abl tyrosine kinase target motif.

DETAILED DESCRIPTION OF THE INVENTION

Figures 1A, 1B:
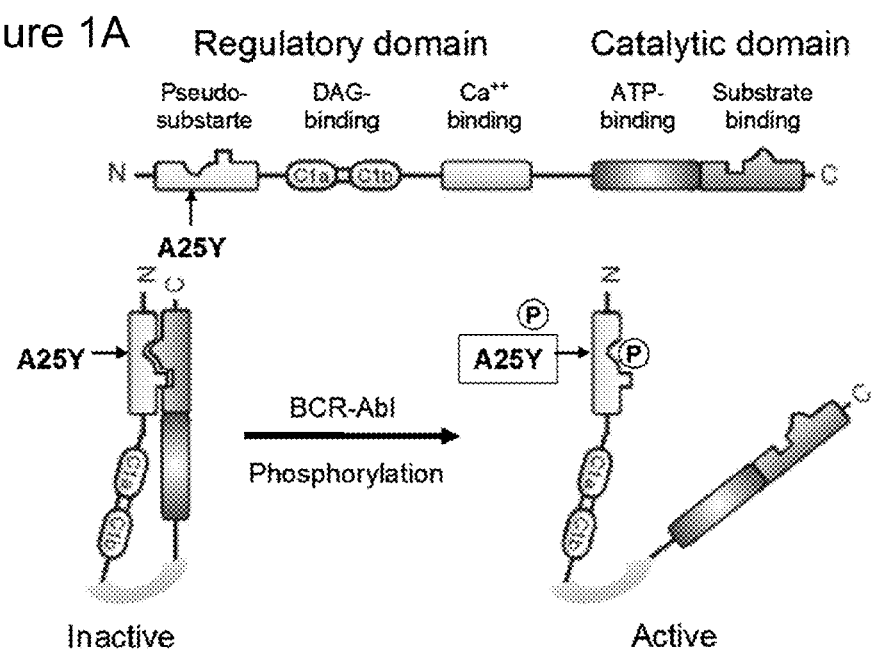
FIG. 1A presents a diagrammatic representation of PKC βII showing A25Y mutation in the pseudosubstrate domain. (Spitaler & Cantrell, *Nat. Immunol.* 2004)
FIG. 1B presents partial amino acid sequence of the wild type PKC bII and A250Y mutants. Sequences depicted in FIG. 1B are: WT (SEQ ID NO:1); A1-2 (SEQ ID NO:2); A2-1 (SEQ ID NO:3); A3-4 (SEQ ID NO:5); A4-6 (SEQ ID NO:5).

The present invention provides compositions and methods for inhibiting the growth of cancer cells in an individual. The method comprises administering to an individual in need of treatment a pro-drug, wherein the pro-drug is a substrate for an enzyme, where the enzyme is endogenous to the cancer cells, and wherein the enzyme is preferentially or exclusively expressed by the cancer cells relative to non-cancer cells. The enzyme that is preferentially or exclusively expressed by the cancer cells relative to non-cancer cells is accordingly considered to be a cancer cell specific enzyme. Conversion of the pro-drug to the active drug by the cancer cell specific enzyme results in inhibition of the growth of the cancer cells. It will be recognized therefore that the present invention is distinct from known methods of gene directed enzyme prodrug therapy (GDEPT) which seek to experimentally alter cancer cells so as to express an exogenous enzyme that activates a pro-drug in the cancer cells.

In various embodiments, the cancer cells inhibited by the method of the present invention may be cancer cells present in solid tumors, or cancer cells present in blood, such as leukemia cells.

In one embodiment, the cancer cell specific enzyme is the Bcr-Abl protein, which exhibits constitutively active Abl tyrosine kinase activity and is expressed in cancer cells comprising a reciprocal chromosomal translocation t(9;22)(q34; q11). The amino acid sequence of the Bcr-Abl protein is known to those skilled in the art, and the skilled artisan can readily determine whether or not a particular cell type obtained from an individual displays constitutively active Abl tyrosine kinase activity. Thus, in one embodiment, the method entails inhibiting growth of cancer cells in an individual, wherein the cancer cells express constitutively active Abl tyrosine kinase activity. In one embodiment, expression of Abl tyrosine kinase is necessary for survival of the cancer cells.

The reciprocal chromosomal translocation known to those skilled in the art by the conventional designation: t(9;22)(q34; q11) is found in, for example, Chronic myeloid leukemia (CML) cells, and the hallmark of CML is the bcr-abl fusion gene, which arises from this reciprocal chromosomal translocation t(9;22)(q34;q11) and results in expression of the chimeric Bcr-Abl protein. The protein is constitutively active in and is believed to be responsible for leukemogenesis.

It is notable that normal (or wild type) PKC is not a substrate for, nor is it directly activated by, tyrosine kinases. However, we demonstrate in the present invention that engineering the Abl kinase target motif into the PKC βII molecule allows the catalytic activity of Bcr-Abl to cross-activate the PKC βII signaling pathway, resulting in direct induction of PKC-mediated cellular responses (differentiation/growth arrest/apoptosis).

Our results indicate that our modified PKC βII molecules are activated in the Bcr-Abl+ CML line K562, but not in the Bcr-Abl− AML cell line KG1a. Our modified proteins also undergo tyrosine phosphorylation and inhibit the expansion of CML blast numbers. Thus the invention is expected to be particularly useful for therapy of malignancies such as CML, where resistance to tyrosine kinase inhibitors is due (in part) to an amplified signal—or in other malignancies where the oncogenic signaling pathway is on but blocking it has no effect (i.e. epidermal growth factor receptor signaling). Further, in contrast to signaling inhibitors, the strategy employed by the present invention utilizes aberrant oncogenic signaling to activate prodrug effector molecules, which can facilitate a cascade effect of a small level of activation at the top of the pathway into a large downstream effect. Also, in contrast to kinase inhibitors, resistance mechanisms that amplify the targeted signaling pathway would actually enhance the efficacy of rewired signaling molecules. Finally, the method of the invention is not dependent on whether the targeted signaling pathway is important for the survival of the malignant cell (unlike small molecule inhibitors), but only that it is on. We also demonstrate that use of a recombinant PKC protein comprising the Abl phosphorylation site, when fused to a cellular transduction domain, is capable of entering cells, thus supporting use of the protein in therapeutic applications.

In a specific embodiment, the pro-drug is a protein kinase C (PKC) Amino acid sequences of human PKCs are well known in the art. While any PKC is expected to be suitable for use in the invention, in one embodiment, the PKC is a PKC βII isoform. An exemplary wild type human PKC βII isoform sequence is provided in SEQ ID NO:8.

A wild type PKC is modified according to the invention so as to comprise the Abl kinase target motif (Ala-X-X-Ile-Tyr-X-X-Phe/Pro (SEQ ID NO:6). Without wishing to be bound by theory, it is believed that the modified PKC, such as a modified human PKC βII, can exploit the catalytic activity of Bcr-Abl in, for instance, human CML cells, to phosphorylate and thereby activate the PKC βII signaling pathway, resulting in induction of PKC-mediated cellular responses (which can include but are not necessarily limited to differentiation/growth arrest/apoptosis) of the cells. The invention therefore provides in one embodiment a method for inhibiting growth of CML cells in an individual comprising administering to the individual a modified PKC βII protein, wherein the protein comprises an Abl tyrosine kinase target motif.

In one embodiment, the invention provides a composition comprising the pro-drug, wherein the pro-drug is a modified PKC βII protein comprising an Abl tyrosine kinase target motif. Also provided are polynucleotides encoding modified PKC βII proteins. Those skilled in the art will recognize that the compositions of the invention are useful not only for therapeutic purposes as set forth in the description of the method of the invention, but also for studying the metabolic and other characteristics of cancer cells, and in particular leukemia cells that express an Abl tyrosine kinase, where that expression at least in part distinguishes the cancer cells from other non-malignant cells.

In addition to the Abl kinase target motif, various other modifications may be made to the PKCs provided by the invention.

In one embodiment, the invention provides the pro-drug as a recombinant protein, wherein the protein comprises a protein transduction domain. The transduction domain can be one which enhances the capability of the protein to enter cells. In one embodiment, the transduction domain is the HIV-TAT domain. Those skilled in the art will recognize that "TAT" represents "Trans-Activator of Transcription", and that HIV-TAT proteins generally have a length of between 86 and 101 amino acids, dependent upon which HIV subtype encodes the particular TAT protein in question. However, the TAT proteins have in common a cellular transduction domain having the sequence YGRKKRRQRRR (SEQ ID NO:7). Thus, in one embodiment, the modified proteins of the invention comprise a cellular transduction domain that comprises or consists of SEQ ID NO:7. Non-limiting examples of sequences that can comprise the TAT domain are shown in SEQ ID NOs:15, 16, 17 and 18, wherein the TAT domain is present at amino acid positions 39-50 in each sequence, but wherein the amino acids at positions 1-38 may also include TAT protein sequences, or other sequences, such as sequences for use in isolating and/or purifying the protein. Therefore, the present invention includes but is not limited to compositions and methods which include proteins comprising the amino acid sequences depicted in SEQ ID NOs:15, 16, 17 and 18, with the proviso that the inclusion of amino acid sequences in positions 1-38 of these sequences is optional. For instance, HIS tag sequences, such as the His shown at positions 5-10 in each of these sequences, are optional (as is the entire amino acid sequence, and any portion thereof, from position 1-38 in each of these sequences). Thus, the invention provides compositions and methods that involve proteins that may begin at their N-terminus at position 39 in SEQ ID NOs:15, 16, 17 and 18.

The proteins provided by the invention also optionally comprise amino acid sequences that constitute reporter proteins. Many reporter genes encoding reporter proteins are known to those skilled in the art and are suitable for use in the invention. In one embodiment, the proteins of the invention comprise a green fluorescent protein (GFP) sequence. For instance, in SEQ ID NOs:15, 16, 17 and 18, the amino acids in positions 757 through the C-terminus comprise a GFP sequence. As such, they represent optional amino acid sequences that may or may not be present in the proteins provided by the invention. Thus, in various embodiments, a protein of the invention comprises an amino acid sequence shown in SEQ ID NOs:15, 16, 17 and 18, with the proviso that the amino acids 1-38 and 757 through the C-terminus are optional and may or may not be present in the proteins. The protein of the invention may therefore comprise or consist of an amino acid sequence having its N-terminus at amino acid position 39 in SEQ ID NOs:15, 16, 17 or 18, and may further comprise the contiguous amino acids of SEQ ID NOs:15, 16, 17 or 18 from position 39 up to amino acid 756, inclusive, in said sequences. Further, such proteins may comprise or consist of an amino acid sequences having its N-terminus at amino acid position 1-39, inclusive, in SEQ ID NOs:15, 16, 17 or 18, which proteins may have at their C-termini amino acid 756 in said proteins, or which may comprise or consist of the entire amino acid sequence shown in SEQ ID NOs:15, 16, 17 or 18.

It will be recognized that the modified proteins provided by the invention as described supra also comprise the Abl kinase target motif (Ala-X-X-Ile-Tyr-X-X-Phe/Pro (SEQ ID NO:6). In various embodiments, the Abl kinase target motif can be present starting at position 21 in the PKC βII protein, such as is shown in the SEQ ID NOs: 10-13 and 14-18, although those skilled in the art that the location of the Abl kinase target motif can be positioned in other places in the protein, so long as the protein remains being capable of activation when phosphorylated by the Abl kinase. In various embodiments, the Abl kinase target motif can be any of SEQ ID NO:2, SEQ ID NO:3, SEQ ID NO:4 or SEQ ID NO:5.

In one embodiment, the invention provides a modified PKCβII, wherein the modified PKCβII is present in a leukemia cell, such as a CML cell, wherein the modified PKCβII is phosphorylated on a tyrosine present in the Abl tyrosine kinase target motif. In one embodiment, the phosphorylated Tyr is the fifth amino acid in the Abl tyrosine kinase target motif.

Compositions comprising the pro-drug may be prepared by mixing the pro-drug with any suitable pharmaceutically acceptable carriers, excipients and/or stabilizers. Some examples of compositions suitable for mixing with the pro-drug can be found in: *Remington: The Science and Practice of Pharmacy* (2005) 21st Edition, Philadelphia, Pa. Lippincott Williams & Wilkins.

It is expected that the pro-drug can be delivered to an individual in need of treatment using any available method and route suitable for pro-drug delivery, including oral, parenteral, subcutaneous, intraperitoneal, intrapulmonary, and intranasal. Parenteral infusions include intramuscular, intravenous, intraarterial, intraperitoneal, and subcutaneous administration. Those skilled in the art, given the benefit of the present disclosure, will be able to determine an effective amount of the modified protein to administer to the individual based on such factors as the age, sex, and size of the individual and the state of the disease.

In one embodiment, a composition comprising the pro-drug is administered to an individual who is diagnosed with, suspected of having, or at risk for developing leukemia. In one embodiment, the leukemia is Chronic myeloid leukemia (CML).

Administration of the pro-drug can be performed in conjunction with conventional therapies that are intended to treat a disease or disorder associated with activated Abl kinase. For example, the pro-drug could be administered prior to, concurrently, or subsequent to conventional anti-cancer therapies. Such therapies can include but are not limited to chemotherapies, surgical interventions, and radiation therapy.

The following Examples are meant to illustrate but not limit the present invention.

EXAMPLE 1

This Example illustrates one embodiment of the present invention, whereby growth of CML cells is inhibited via administration of a pro-drug to the cells in the form of a genetically modified PKC βII comprising the Abl kinase target motif (Ala-X-X-Ile-Tyr-X-X-Phe/Pro), wherein the CML specific enzyme Bcr-Abl phosphorylates the PKC βII prodrug to convert it to an activated drug form, thereby causing PKC-mediated inhibition of the growth of the CML cells.

Construction of A25Y PKC βII mutants. Substitution of Ala$^{25}$ with the phosphomimetic residue Glu results in a constitutively active PKC. We tested whether mutation of Ala$^{25}$ in the auto-inhibitory pseudosubstrate domain of PKC βII to a phosphorylatable tyrosine (A25Y) within an Abl target motif would, upon direct Bcr-Abl phosphorylation, introduce a negative charge and cause disassociation of the pseudosubstrate domain from the catalytic site, resulting in PKC βII activation (FIG. 1A). This Bcr-Abl-activated PKC βII signaling should then induce cellular responses, potentially including blast differentiation/growth arrest/apoptosis. Kharfan-Dabaja, M. A., Ayala, E., Guller, I., Cejas, P. J., Bahlis, N. J., Kolonias, D., Carlson, L. M., and Lee, K. P. Differentiation of acute and chronic myeloid leukemia into functional dendritic cells: a comparative analysis of different signaling mechanisms. Cancer Immunol Immunother. 2005, 54 (1): p. 25-36 Lindner I, Kharfan-Dabaja M A, Ayala E, Kolonias D, Carlson L M, Beazer-Barclay Y, Scherf U, Hnatyszyn J H, Lee K P. Induced dendritic cell differentiation of chronic myeloid leukemia blasts is associated with down-regulation of BCR-ABL. J. Immunol. 2003 Aug. 15; 171(4):1780-91.

The native PKC βII core pseudosubstrate sequence is Arg-Phe-Ala-Arg-Lys-Gly-Ala-Lys-Arg-Gln-Lys-Asn-Val (WT, FIG. 1B; sequence identifiers are as shown in FIG. 1B). We used oligonucleotide primers/PCR to convert the underlined sequence to the following Bcr-Abl target motifs (changes from the native sequence in bold italics, tyrosine is the phosphorylated residue): clone A1-2 (Ala-Arg-Lys-Ile-Tyr-Lys-Arg-Pro), clone A2-1 (Ala-Arg-Lys-Ile-Tyr-Lys-Arg-Phe (Phe more closely resembles the Gln it is replacing than does Pro)), clone A3-4 (Ala-Arg-Lys-Ile-Tyr-Lys-Arg-Thr (Thr being a polar/uncharged residue like Gln it replaces)) and clone A4-6 (Ala-Arg-Lys-Ser-Tyr-Lys-Arg-Phe (Ser being a polar/uncharged residue like the Gly it replaces. We have made these A25Y (A25Y) mutants in PKC-βII-GFP, which is PKC βII genetically fused to GFP (which does not affect its PKC activity). The GFP tag allows for direct visualization of enzyme activation by membrane translocation, and also is bigger than the endogenous enzyme as determined by Western blot.

Figure 2:
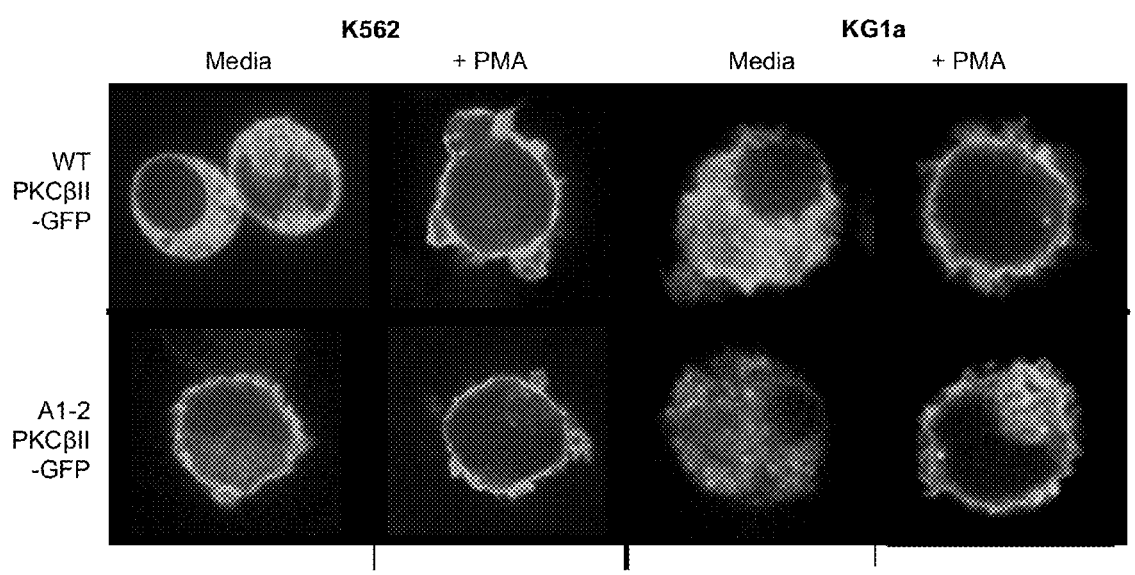
FIG. 2 presents a confocal miscroscopy analysis wherein the wild type (WT) or A25Y A1-2 PKC βII-GFP clone were transiently transfected into K562 (Bcr-Abl+) or KG1a (Bcr-Abl−) and after 24 hr visualized by confocal microscopy for the GFP tag after no treatment (media) or PMA treatment for 30 minutes.

Selective activation of A25Y PKC βII-GFP in the Bcr-Abl-positive CML cell line K562. Activation of PKC βII results in translocation of the enzyme from the cytosol to the plasma membrane, and this can be tracked in the wild type (WT) or A25Y PKC βII-GFP mutants by confocal microscopy imaging of the GFP tag. These constructs were nucleofected (Amaxa) into the Bcr-Abl-positive CML cell line K562 or the Bcr-Abl-negative AML cell line KG1a, and transfectants left untreated (media) or PMA treated. As seen in FIG. 2, the parental PKC βII-GFP does not translocate in either K562 or KG1a unless stimulated by the PKC agonist PMA. This indicates that if there is any indirect activation of PKC βII by Bcr-Abl in the untreated K562, it is happening at a level too low to detect by this approach. In contrast, the A2-1 A25Y PKC βII-GFP mutant is translocated to the plasma membrane in K562 cells in the media-only condition, and further activated by PMA addition (indicating the mutated PKC is still responsive to PKC activation stimuli). However, it is not activated in Bcr-Abl-negative KG1a cells unless PMA is added. By confocal imaging we have found that three constructs are activated in K562 but not KG1a (two clearly (clones A1-2, A-3-4) and 1 less strongly (A2-1)), while the fourth (A4-6) appears to be constitutively active. These findings indicates that 3 of the A25Y PKC βII-GFP constructs are being activated by Bcr-Abl.

Figure 3:
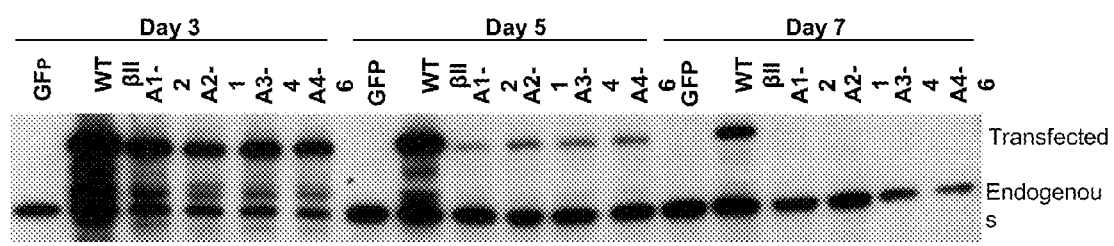
FIG. 3 provides a photographic representation of an electrophoretic analysis of the expression of the wild type and A25Y PKC βII-GFP protein in K562. K562 cells were transiently transfected with GFP only, wild type PKC-βII-GFP, or the mutated A25Y constructs. Transfections were performed by Amaxa nucleofection, with the transfection efficiency for the constructs ranging from 83-90%. At the timepoints indicated, cells were lysed and equal amounts of protein were analyzed for PKC βII expression by Western blot.

Evidence of activation-induced PKC degradation. We examined whether activation of PKC βII-GFP protein results in its degradation and loss, a general characteristic of the PKC family, in the transfected K562 in media alone, with the prediction that ongoing Bcr-Abl activation of the A25Y PKC βII-GFP may cause more rapid loss of these proteins vs. WT PKC βII-GFP. It should be noted that the transfection efficiency of K562 cells by Amaxa nucleofection was uniformly high (83-90%) for all the constructs. The expression of wild type PKC βII-GFP and A25Y PKC βII-GFP (which are larger than the endogenous PKC βII) over time in K562 cells was assessed by Western blot (FIG. 3). 24 hours after transfection there are equivalent protein levels of WT PKC-βII-GFP vs. the A25Y PKC βII-GFP mutants (see FIG. 4, bottom panel). Also, at a 16 hr time point there was a similar amount of GFP expression (by flow cytometry) between WT and mutant A25Y PKCβII transfectants (data not shown). However, by day 3 there is substantially less A25Y vs. WT PKC βII-GFP. And although there is some loss of WT PKC βII-GFP expression over time, the expression of the A25Y PKC βII-GFP protein is more rapidly lost—for example, A1-2 expression on day 3 vs. day 5 compared to WT βII expression on day 5 (which is similar to A1-2 expression on day 3) vs. day 7. This differential effect makes it unlikely this is due to non-specific loss of the plasmids, and two non-mutually exclusive possibilities for accelerated loss of A25Y PKCβII expression are increased PKC activation (by Bcr-Abl activation) and/or growth suppression/killing of the transfected cells.

Figure 4:
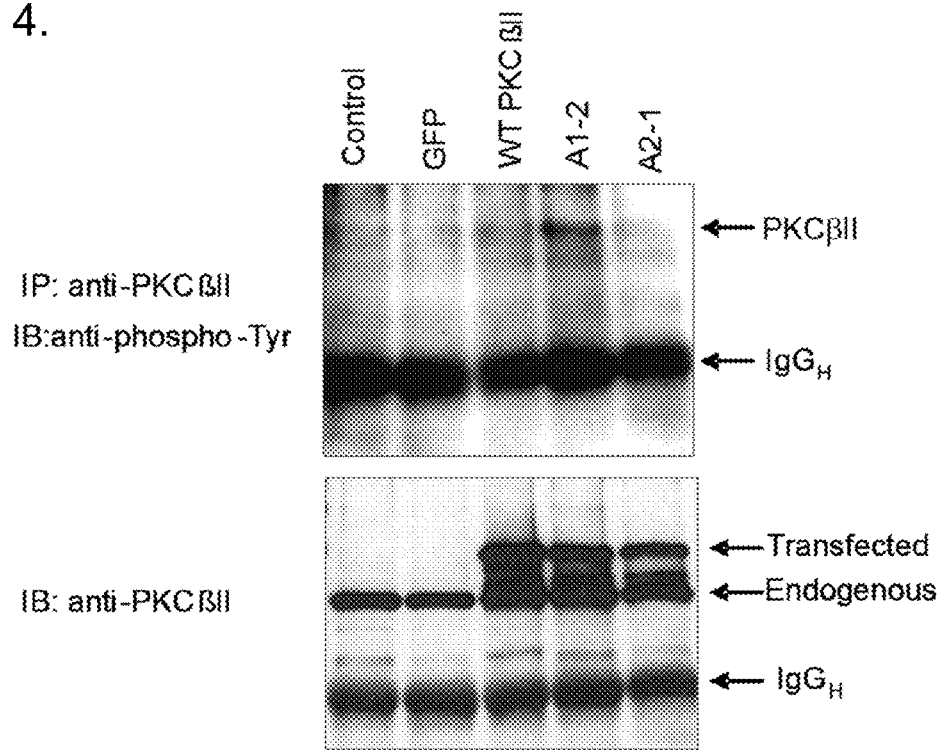
FIG. 4 provides a photographic representation of electrophoretic analysis of tyrosine phosphorylation of the A25Y PKC βII-GFP clones. K562 cells were transfected with GFP, WT-PKC βII-GFP or A25Y PKC βII-GFP clones and 24 h later, cell extracts were immunoprecipitated (IP) with anti-PKC βII antibody followed by immunoblotting (IB) with anti-phospho-tyrosine (upper panel) The blot was stripped and reprobed with anti-PKC βII to confirm equal loading (lower panel).

Tyrosine phosphorylation of A25Y PKC βII-GFP mutants. Plasma membrane translocation and loss of protein expression suggest that the A25Y PKC βII-GFP mutants are being activated in K562, but do not indicate how. In addition to Bcr-Abl-mediated activation, it is formally possible that they are constitutively active (which would result from any significant structural disruption of the pseudosubstrate domain, and as we suspect for the A4-6 construct), have a lower activation threshold for the traditional PKC second messengers, or are being activated via some other signaling pathway. If the A25Y PKC βII mutants are being activated by Bcr-Abl, the engineered tyrosine should be phosphorylated. To assess this, K562 cells were transfected with GFP, WT-PKC βII-GFP and clones A1-2 (which clearly translocates in K562 (in media) by confocal) and A2-1 (which translocates less well). 24 h later, cell extracts were immunoprecipitated with anti-PKC βII antibody, and then phosphorylation was assessed by western blot analysis with phospho-tyrosine antibody. As seen in FIG. 4 (top panel), there is no evidence for tyrosine phosphorylation of endogenous PKC βII (for example, in the control and GFP transfection lanes), of WT PKC βII-GFP (also indicating that tyrosine residues in the GFP tag is not being phosphorylated), or (somewhat unexpectedly) of the A2-1 clone. The A1-2 clone is clearly tyrosine phosphorylated—and given this clone differs from the WT PKC-βII-GFP in tyrosine content only at the engineered Abl-target motif, it is likely that it is the Tyr$^{25}$ that is being phosphorylated. The bottom panel (FIG. 4) demonstrates that similar amounts of PKC βII-GFP were immunoprecipitated in all 3 PKC transfectants (the IgG$_H$ band is from the original IP, identified on Western blot by the secondary antibody).

Figure 5:
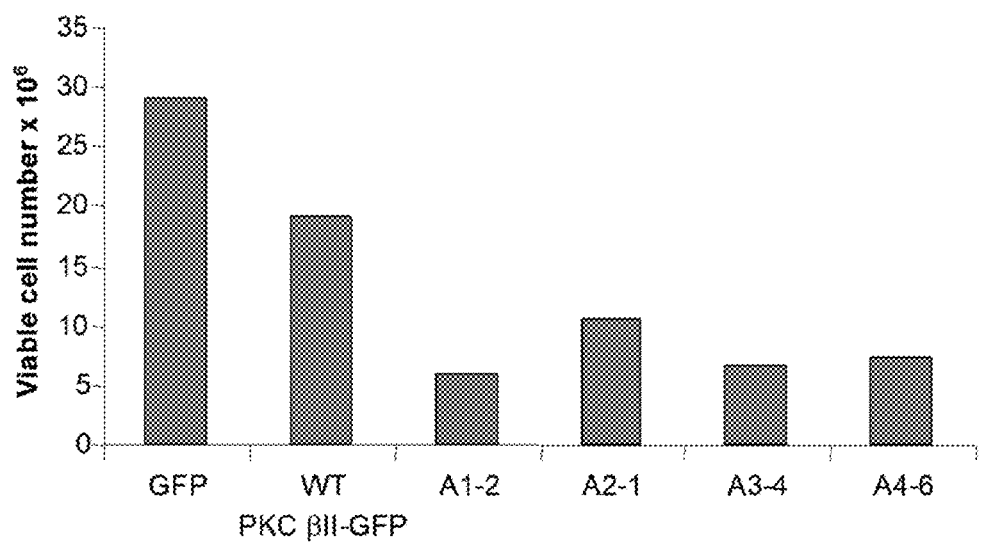
FIG. 5 provides a graphical representation of data obtained from analysis of cell expansion. K562 cells were transfected with GFP alone, wild type PKC bII-GFP or the mutated A25Y constructs. Three million cells were plated in culture, and viable cell numbers counted after 7 days.
Figure 6:
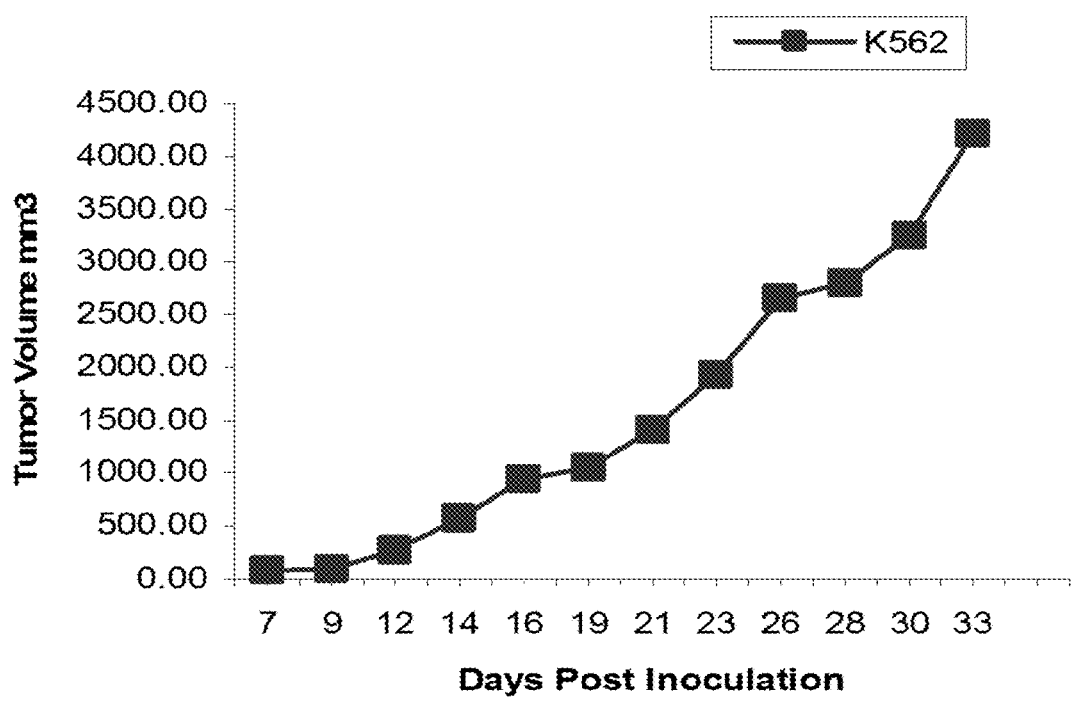
FIG. 6 provides a graphical representation of data obtained from analysis of tumor growth in mice. $10 \times 10^6$ K562 cells were inoculated SQ in NOD/SCID mice and tumor growth was monitored at indicated time points.

Transfection of A25Y PKC βII mutants reduces the growth of K562 cells. To assess the effect of A25Y PKC βII-GFP on cell expansion, equal numbers of transfected K562 were plated in media alone and counted after 7 days (FIG. 5). There is some inhibition of cell expansion by the WT PKC βII-GFP vs. GFP-only transfected K562, with substantially greater inhibition by the A25Y PKC βII-constructs. Thus, this Example demonstrates inhibiting growth of cancer cells comprising administering to the cells a pro-drug, wherein the pro-drug is a substrate for an enzyme, wherein the enzyme is endogenous to the cancer cells, and wherein the enzyme is exclusively expressed by the cancer cells relative to non-cancer cells, wherein the pro-drug is converted to a drug by the enzyme, and wherein the growth of the cells is inhibited by the drug subsequent to conversion of the pro-drug to the drug.

EXAMPLE 2 pTAT-A25Y PKC βII-GFP Construct

This Example demonstrates development of pTAT-A25Y PKC βII-GFP construct for use in delivering the prodrug to cells.

In order to deliver the A25Y PKC βII-GFP proteins to cells and in vivo, we cloned the cDNA constructs into the pTAT-HA vector, which adds the HIV TAT transducer domain (plus the HA tag) to the N terminus of the A25Y PKC βII-GFP. The incorporated HIV TAT transducer domain has been shown to allow large proteins to readily cross cell membranes and diffuse intracellularly in vitro and in vivo. This vector can be transformed into bacteria and production of the encoded protein induced by the addition of IPTG. This construct also introduces 6 histadines (His6) into the protein that allows for purification of the protein over a nickel bead column, as well as an HA tag that allows for the Western blot analysis for this epitope. The pTAT cector was digested with XhoI and filled in to blunt the 3' cloning end, the 5' end was digested with KpnI and the A25Y PKC βII-EGFP cDNA insert was double digested with KpnI and NaeI and ligated into the pTAT vector digested with KpnI and blunted at XhoI site.

In addition, the TAT-A25Y-PKC βII-GFP insert was subcloned into the eukaryotic expression vector pcDNA3, which allows us to transfect the construct into cells and determine if it remains active despite the addition of the TAT-HA elements to the protein (see below).

Functional Assessment of TAT-A25Y PKC βII-GFP.

Figure 7:
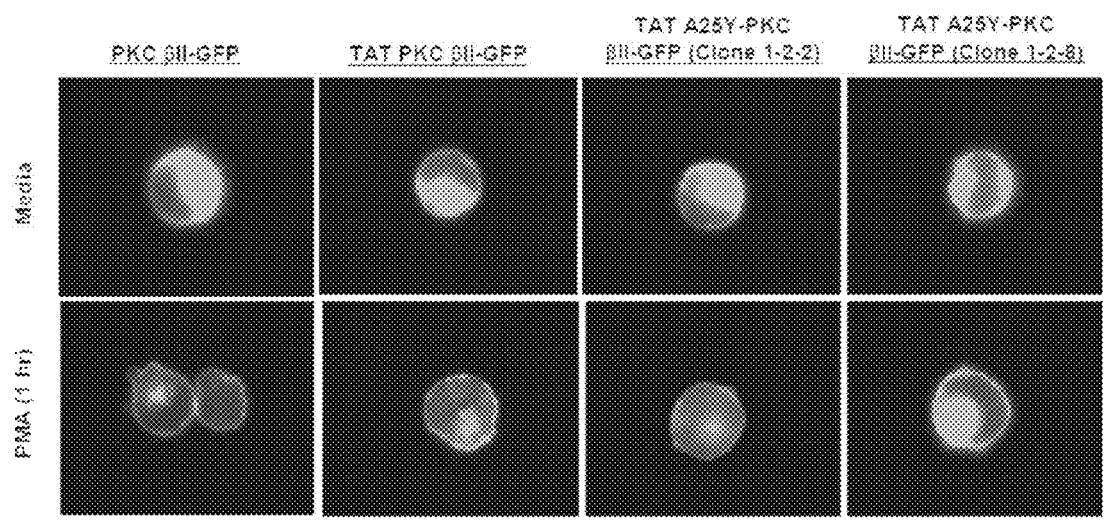
FIG. 7 provides a fluorescent microscopy analysis of pTAT cDNA clones nucleogected in Bcr-Abl+ K562 cells. After 24 hours cells were imaged by fluorescent microscopy in media alone, or 1 hour after the addition of the PCT agonist PMA.

Because the addition of the TAT-HA domains to the N terminus of the A25Y-PKC βII-GFP proteins has the potential to disrupt the protein's structure adjacent to the pseudosubstrate domain, it is possible that this addition results in a constitutively active protein that no longer requires activation by PKC agonists (PMA in our experiments) or Bcr-Abl. Conversely, these modifications may prevent activation altogether. To test this, we transfected the TAT-A25Y-PKC βII-GFP constructs in the pcDNA3 vector into the Bcr-Abl+ CML cell line K562. K562 cells were split to 0.5×106 cells/ml 20-24 hours before transfection. 2×106 cells per sample to be transfected were spun down at 850 RPM for 10 min. The cells were then resuspended in 100 µl of Amaxa Reagent V plus supplement per sample and mixed with 5-10 µg of DNA. Cells were then transfected using Amaxa protocol T-16 and then transferred to a 6 well plate containing 2 mls of media prewarmed to 370. After 3-4 hours of being incubated at 370 3 mls of media were added to each well and continued to be incubated for 24-48. Translocation of the PKC βII enzyme from the cytoplasm to the plasma cell member is indication that the enzyme has been activated, and with our TAT-A25Y-PKC βII-GFP proteins can be followed on the basis of the fluorescent GFP tag using fluorescent microscopy to determine subcellular localization. As seen in FIG. 7, compared to the control parental PKC βII-GFP, there appears to be no constitutive activation of TAT-PKC βII-GFP under media conditions indicating that addition of the TAT-HA did not disrupt the regulatory pseudosubstrate domain.

The two TAT-A25Y-PKC βII-GFP clones (A1-2-2 and A1-2-8) show some activation in the K562, which we believe is due to Bcr-Abl-mediated activation. For all the constructs, there is significant activation with the PKC agonist PMA, indicating that the TAT-PKC βII-GFP clones are still responsive to appropriate activation signals. Together, these data indicate that adding the TAT-HA domain does not affect the behavior of the original PKC βII-GFP constructs.

Bacterially Synthesized TAT-A25Y-PKC βII-GFP Protein.

Figure 8:
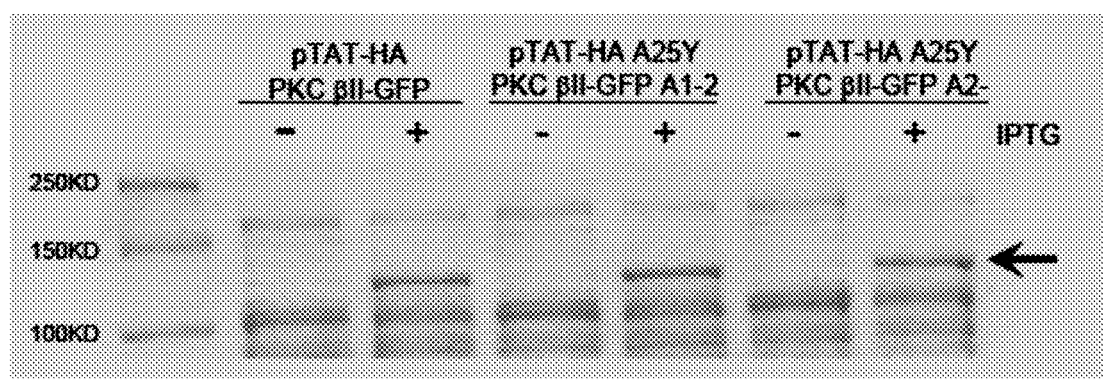
FIG. 8 provides a photographic representation of analysis of bacterial lysates from bacteria (BL21) transformed to express recombinant proteins of the invention. Proteins from cells uninduced (−) or induced with IPTG (+) were analyzed on an 8% gele and stained for proteins. The arrow points to induced proteins of the expected size.
Figure 9:
FIG. 9 provides a photographic representation of fluorescent microscopy analysis of bacterial protein lysates containing TAT-A25Y-PKC βII-GFP transduced into K652 cells (20 h).

To synthesize the TAT-A25Y-PKC βII-GFP protein for administration, the pTAT constructs were transformed into competent BL21(DES) cells and plated on LB agar+carbanicillin plates and grown overnight at 370. A 5 ml culture (LB+carb) was inoculated with a single colony of BL21 (DES) transformed cells and grown overnight at 370. The overnight culture was used to inoculate 50 mls of LB+ carb. Bacteria were grown to an O.D. of 0.6 and then induced with IPTG at a concentration of 1 mM and grown overnight at 370 with shaking. The cells were pelleted in 15 ml aliquots by centrifuging at 3500 RPM for 15 minutes. The cell pellets were either frozen at −800 or directly lysed. The bacterial pellet was lysed in 3 mls of lysis buffer+lysozyme added at 1 mg/ml and incubated on ice for 30 minutes. Lysates were then sonicated for 6 cycles of 10 seconds—sonication/10 seconds on ice. Proteins were concentrated using a Viva Spin column (30,000 MW cut off) with 3 washes of PBS. The protein lysates were then analyzed by on a Comassie gel (FIG. 8), which demonstrates bacterial synthesis of the proteins. To determine if the proteins can be transduced into live cells, K562 cells were plated at 0.1×106 cells in 0.5 mls of 10% serum media in a 24 well plate. ~500 µg of total concentrated bacterial induced protein (not additionally purified at this point) for each construct were added to each well. The cells were then incubated overnight at 370. Transduction of the bacterially synthesized TAT-A25Y-PKC βII-GFP protein was then examined by fluorescent microscopy for the GFP tag. As seen in FIG. 9, these proteins are capable of being transduced into cells, even as crude lysates that have not been further purified. These data indicate that we can synthesize recombinant TAT-A25Y-PKC βII-GFP protein that retains the characteristics of the parental A25Y-PKC βII-GFP molecules, and can be delivered to cells via TAT transduction.

EXAMPLE 3

This Example demonstrates that Mutated PKCBII translocates to the plasma membrane in Bcr/Abl+ K562 but not Bcr/Abl− KG1a cells.

Figure 10:
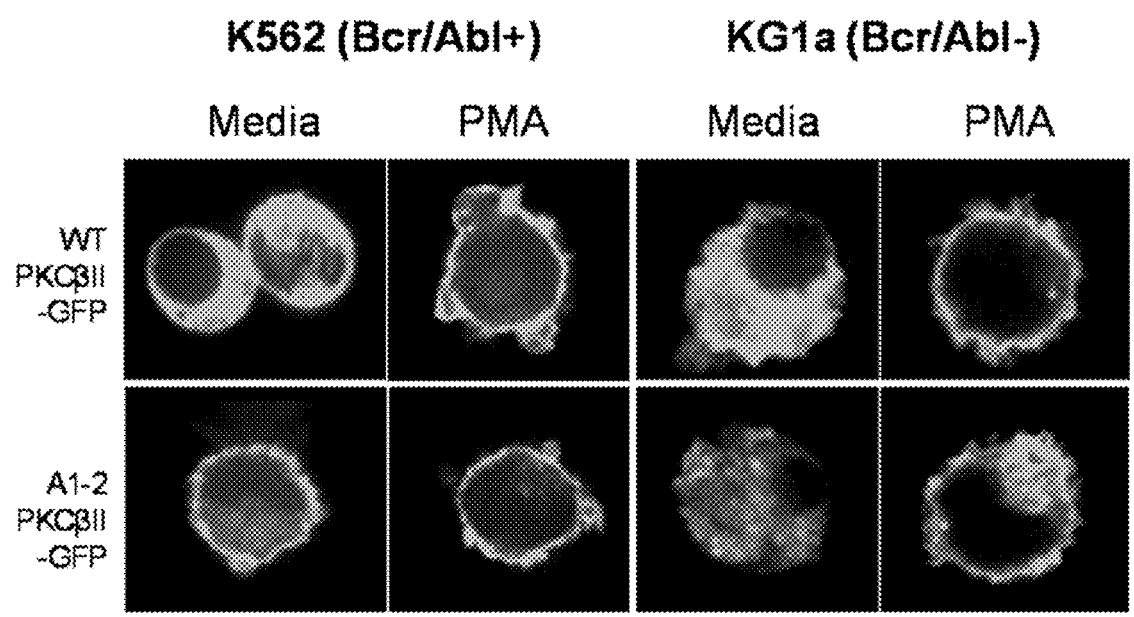
FIG. 10 a photographic representation of confocal microscopy imaging of WT and A1-2 PKCBII-GFP clones 24 hours after transfection into K562 (Bcr/Abl+) and KG1a (Bcr/Abl−) cells. Cells were visualized after no treatment (media) or 30 minutes after PMA treatment.

Upon activation, PKCBII translocates from the cytoplasm to the plasma membrane. To determine the activation status of PKCBII through translocation to the plasma membrane, WT and A25Y PKCBII-GFP mutants were Amaxa nucleofected into K562(Bcr/Abl+) and KG1a (Bcr/Abl−), and then visualized using confocal microscopy either after no treatment in media, or 30 minutes after PKCBII agonist PMA treatment. As seen in FIG. 10, the WT PKCBII-GFP construct is cytosolically localized in media treated Bcr/Abl+, K562 cells; upon addition of PMA however, the enzyme translocates and is primarily localized to the plasma membrane. A similar trend is observed in Bcr/Abl− KG1a cells, where prior to PMA addition WT PKCBII-GFP is localized to the cytosol and only after PMA treatment does it translocate to the plasma membrane. In contrast, the A1-2 A25Y PKCBII-GFP mutant is found primarily at the plasma membrane in media treated K562 cells and is further activated by the addition of PMA, indicating that the A25Y PKCBII-GFP mutants are still responsive to traditional PKC stimuli. In Bcr/Abl− KG1a cells however, the A1-2 A25Y PKCBII-GFP mutant is not activated in media alone, and translocates to the plasma membrane only upon addition of PMA. Analysis of the 3 other A25Y mutants (A2-1, A3-4, and A4-6) revealed that while A2-1 and A3-4 are also activated in K562 but not in KG1a cells, A4-6 might be constitutively active as it is found localized to the plasma membrane in both cell types. These data suggest that at least three of the A25Y mutant constructs are activated in a Bcr/Abl dependent manner.

EXAMPLE 4

This Example demonstrates that transfection of A25Y PKCBII mutants induces apoptosis, and decreases the growth of K562 cells.

Figure 11A:
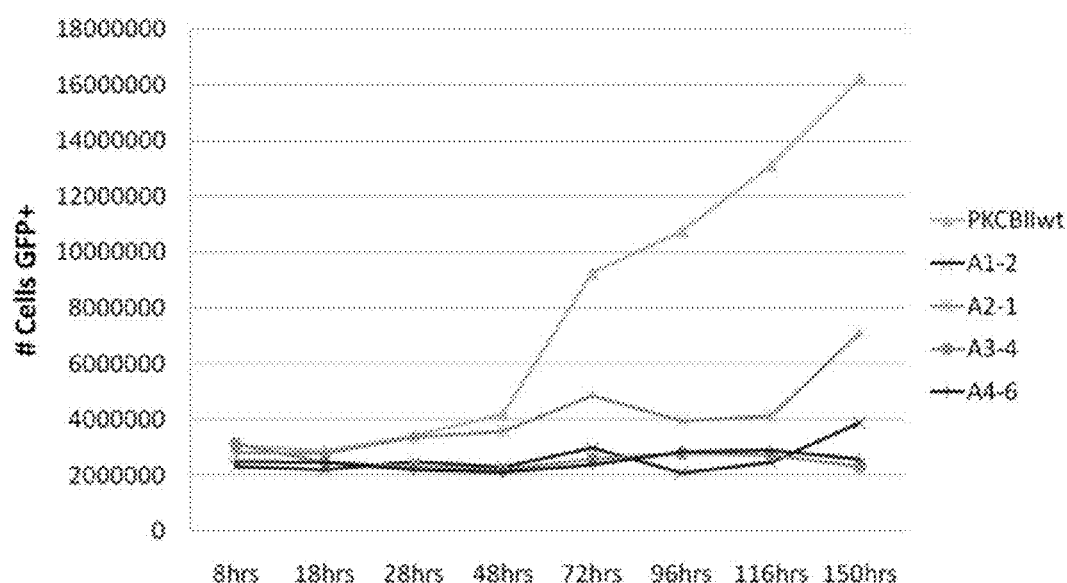
FIGS. 11A and 11B provide graphical representations of data obtained from flow cytometric analysis performed on WT and A25Y transfected K562 cells. Transfected cells were counted and harvested at the indicated time points and stained with AnnexinV-PE for 30 minutes, then measured for expression of GFP (A) and AnnexinV (B) using flow cytometry. AnnexinV+ cells were gated on the GFP+ population.
Figure 11B:
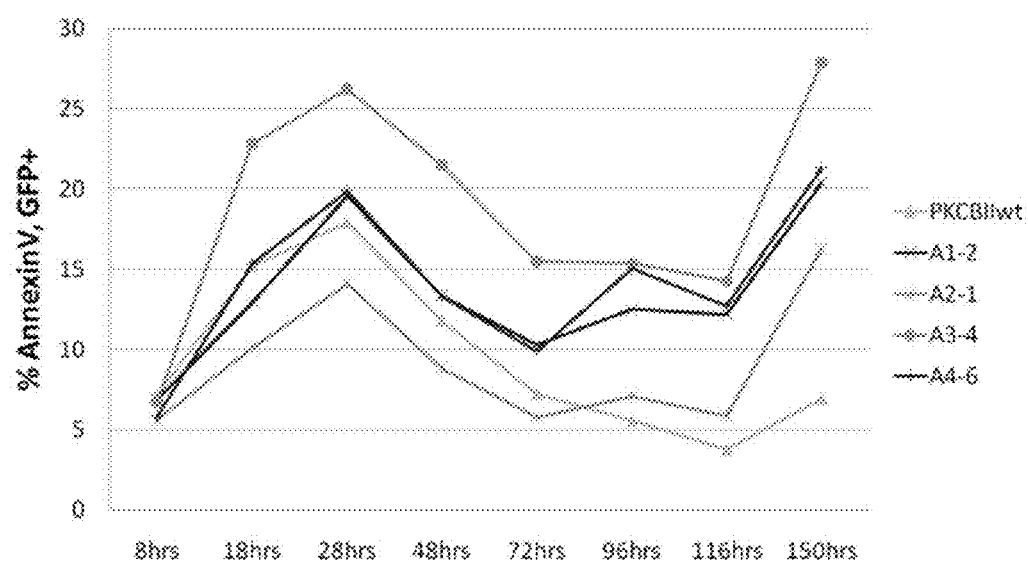

We have demonstrated that activation of PKCBII by PMA induces cellular arrest as well as increases in apoptosis in K562 cells. To determine if activation of A25Y-PKCBII mutants had comparable effects to endogenous PKCBII activation, the four A25Y-PKCBII mutants along with WT PKCBII-GFP were nucleofected (Amaxa) into K562 cells and analyzed for their levels of GFP expression. As seen in FIG. 11A, the number of GFP+ K562 cells that were transfected with WT-PKCBII steadily increases over the course of the experiment, while the number of GFP+ K562 cells that were transfected with A25Y-PKCBII mutant constructs were inhibited in their cellular expansion. To determine if activation of A25Y-PKCBII had any effects on the induction of apoptosis, K562 cells were transfected with WT and A25Y-PKCBII and measured for apoptosis using the AnnexinV-PE antibody. AnnexinV+ cells were gated on the GFP+ population. As seen in FIG. 11B, all GFP+transfected cells showed increases in the level of apoptosis at 18-28 hours after transfection, with A3-4 transfected cells showing the highest level of apoptosis. WT-PKCBII transfected cells also showed an increase in apoptosis in the 18-28 hours after transfection, this level decreased steadily over time. In contrast, the A3-4, A1-2, and A4-6 transfected cells showed higher levels of apoptosis maintained over the course of the experiment. These data suggest that upon activation by Bcr/Abl, A25Y-PKCBII induces cellular arrest and apoptosis. The greatest effect occurred in A3-4 transfected cells.

EXAMPLE 5

This Example demonstrates efficient generation and transmission of TAT-A25Y-PKCBII protein into K562 cells.

Figure 12:
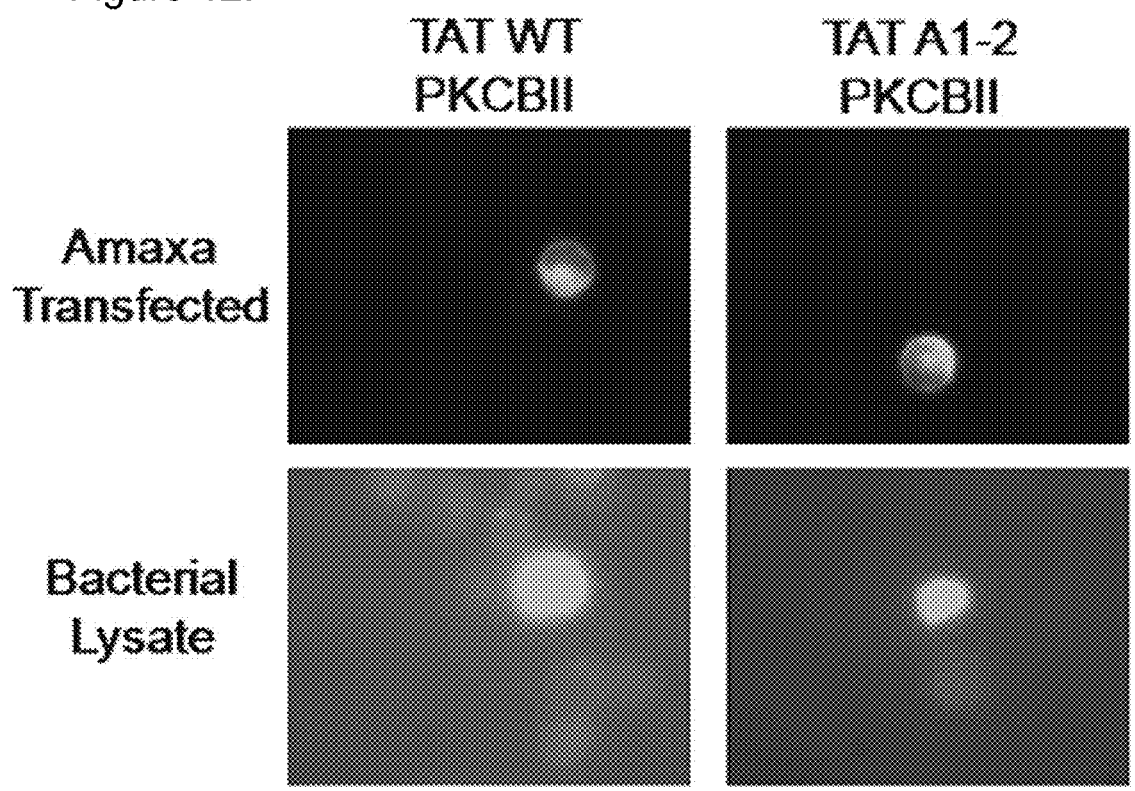
FIG. 12 provides photographic representations of microscopy imaging of both WT and A1-2 TAT-A25Y-PKCBII Amaxa transfected, and bacterial lysate added K562 cells. Bacterial lysates were purified for the TAT-A25Y protein and then added onto K562 cells for 20 hours.

To determine whether or not the addition of the protein transduction domain (PTD) of HIV TAT onto our A25Y-PKCBII mutants would permit transduction into cells, the PTD sequence was added onto the 5' terminus of the A25Y mutants and cloned into E. coli. Purified TAT-A25Y-PKCBII protein was then added to cultures of Bcr/Abl+ K562 cells, and visualized 20 hours later for expression of GFP using microscopy. As seen in FIG. 12, levels of GFP expression between Amaxa transfected cells and purified TAT-PKCBII added cells are equivalent. These data indicate that the TAT-A25Y-PKCBII is taken up by Bcr/Abl+ K562 cells whereupon it is to be likely activated in a similar manner as in Amaxa transfected cells.

While the above invention has been described through specific examples, routine modifications will be apparent to those skilled in the art and such modifications are intended to be within the scope of this invention.

We claim:

1. A method for inhibiting growth of cancer cells in an individual, wherein the cancer cells have constitutively active Abl tyrosine kinase activity, the method comprising administering to the individual a modified protein kinase C (PKC) bII, wherein the modified PCKbII comprises an Abl tyrosine kinase target motif, wherein the Abl tyrosine target motif is the eight amino acid sequence beginning at position 21 in SEQ ID NO:10, through amino acid position 28 in SEQ ID NO:10, wherein the modified PKC bII is phosphorylated by a Bcr-Abl protein expressed by the cancer cells, and wherein the growth of the cancer cells is inhibited subsequent to phosphorylation of the modified PKC bII by the Bcr-Abl protein.

2. The method of claim 1, wherein the modified PKC bII comprises a cellular transduction domain.

3. The method of claim 2, wherein the cellular transduction domain comprises SEQ ID NO:7.

4. The method of claim 1, wherein the individual is an individual diagnosed with, suspected of having, or at risk for developing leukemia.

5. The method of claim 4, wherein the leukemia is Chronic myeloid leukemia (CML).

* * * * *